(12) United States Patent
Canary et al.

(10) Patent No.: US 9,221,744 B2
(45) Date of Patent: Dec. 29, 2015

(54) ASYMMETRIC CATALYSTS

(71) Applicants: James Canary, New York, NY (US); Shahab Mortezaei, New York, NY (US)

(72) Inventors: James Canary, New York, NY (US); Shahab Mortezaei, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/407,124

(22) PCT Filed: Jun. 11, 2013

(86) PCT No.: PCT/US2013/045220
§ 371 (c)(1),
(2) Date: Dec. 11, 2014

(87) PCT Pub. No.: WO2013/188432
PCT Pub. Date: Dec. 19, 2013

(65) Prior Publication Data
US 2015/0112066 A1 Apr. 23, 2015

Related U.S. Application Data

(60) Provisional application No. 61/658,379, filed on Jun. 11, 2012.

(51) Int. Cl.
*C07F 1/08* (2006.01)
*B01J 31/12* (2006.01)
*C07C 201/12* (2006.01)
*B01J 31/18* (2006.01)
*B01J 31/22* (2006.01)

(52) U.S. Cl.
CPC ............. *C07C 201/12* (2013.01); *B01J 31/183* (2013.01); *B01J 31/2295* (2013.01); *C07F 1/08* (2013.01); *B01J 2231/30* (2013.01); *B01J 2231/32* (2013.01); *B01J 2531/0216* (2013.01); *B01J 2531/16* (2013.01)

(58) Field of Classification Search
USPC ............................................ 546/10; 502/165
See application file for complete search history.

(56) References Cited

U.S. PATENT DOCUMENTS 6,541,645 B1   4/2003   Canary et al.
7,024,068 B2   4/2006   Canary et al.

OTHER PUBLICATIONS

Canary et al., "Redox-Reconfigurable Tripodal Coordination Complexes: Stereodynamic Molecular Switches," Chem. Commun. 46:5850-60 (2010).
Dai et al., "Chiroptical Switches: Applications in Sensing and Catalysis," Molecules 17:1247-77 (2012).
Mortezaei et al., "A Redox-Reconfigurable, Ambidextrous Asymmetric Catalyst," J. Am. Chem. Soc. 134:8054-57 (2012).
You et al., "Development of a Family of β-Amino Alcohol Ligands with Two Stereocenters for Highly Efficient Enantioselective Trimethylsilylcyanation of Aldehydes," Chem. Commun. 1963-64 (2000).
International Search Report and Written Opinion for corresponding application No. PCT/US13/45220 (Feb. 10, 2014).

*Primary Examiner* — Charanjit Aulakh
(74) *Attorney, Agent, or Firm* — LeClairRyan, a Professional Corporation

(57) ABSTRACT

The present invention relates to asymmetric catalysts, including redox-reconfigurable asymmetric catalysts. Methods of producing compounds having one or more stereocenters using the asymmetric catalysts of the present invention are also disclosed.

39 Claims, 12 Drawing Sheets

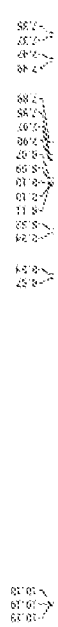
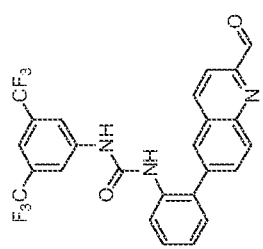
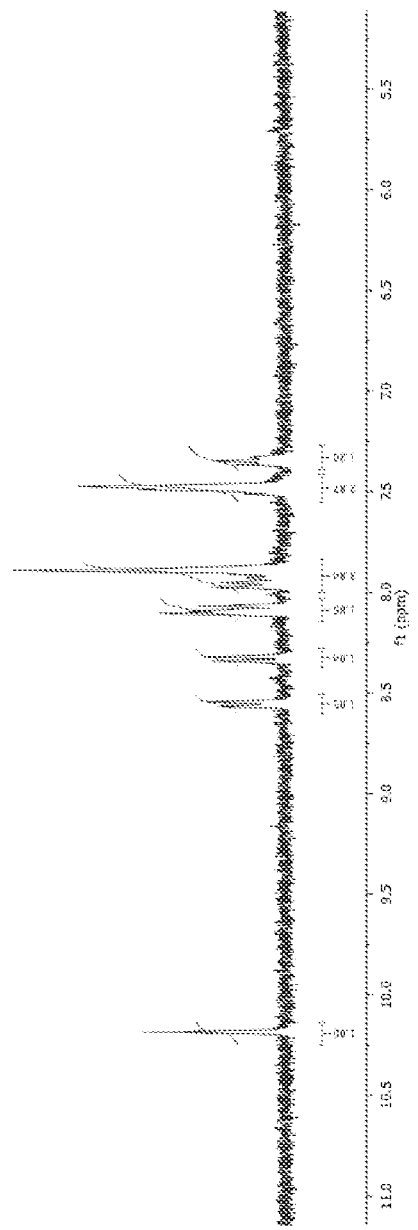
Figure 8

Figures 9A–B

A
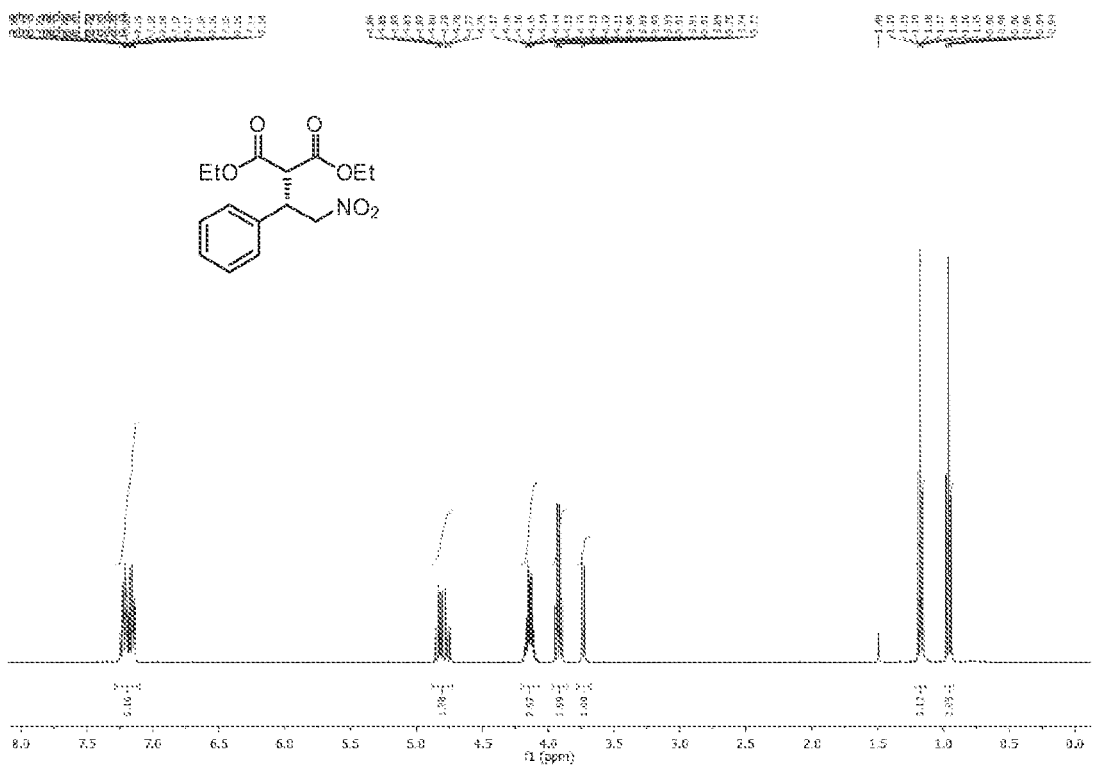
B
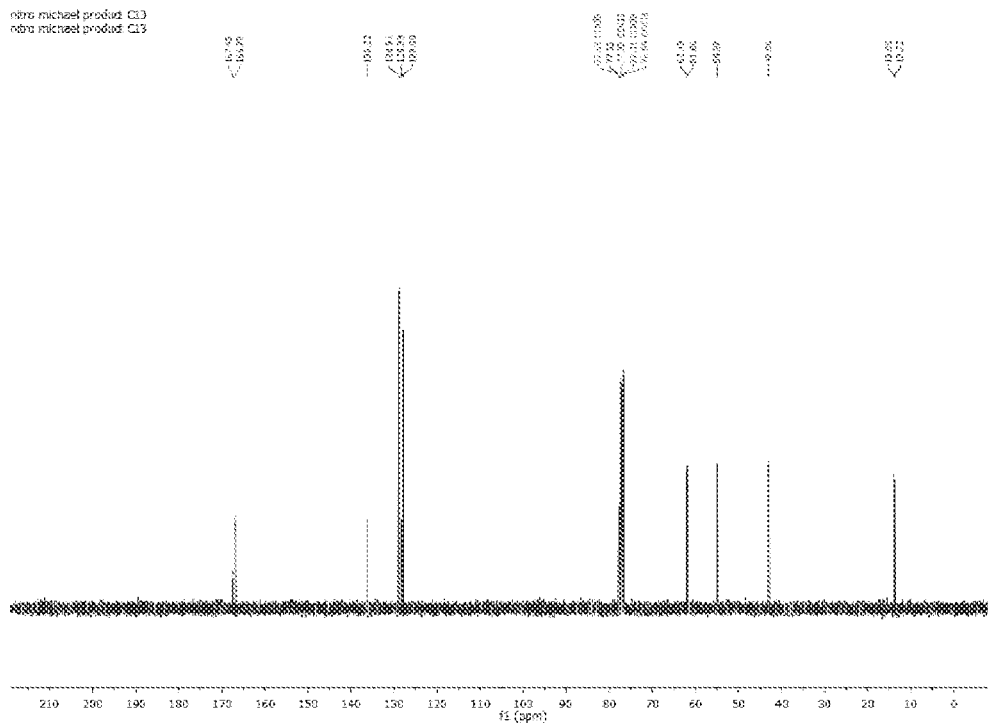
Figures 11A–B

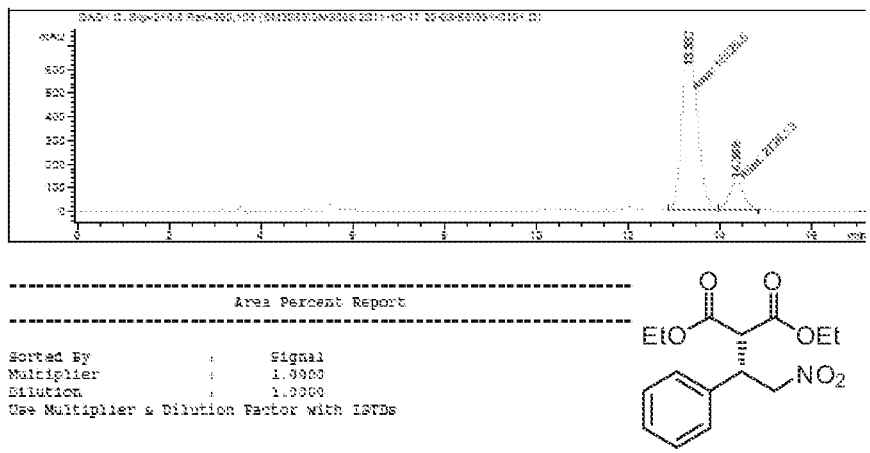
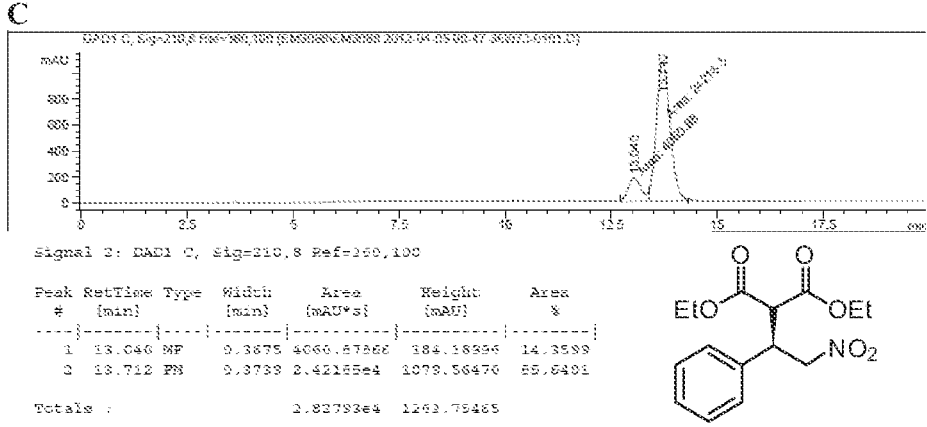
Figures 12B–C

ASYMMETRIC CATALYSTS

This application is a national stage application under 35 U.S.C. 371 of PCT Application No. PCT/US2013/045220, filed Jun. 11, 2013, which claims the benefit under 35 U.S.C. §119(e) of U.S. Provisional Patent Application No. 61/658,379, filed Jun. 11, 2012, which is incorporated herein by reference in its entirety.

This invention was made with U.S. Government support under Grant Nos. CHE-0848234 and CHE-0958457 awarded by the National Science Foundation. The U.S. Government has certain rights in this invention.

FIELD OF THE INVENTION

The present invention relates to ambidextrous asymmetric catalysts, including those that can be reconfigured by reduction/oxidation.

BACKGROUND OF THE INVENTION

Inversion of helicity has long intrigued investigators in a number of fields (Pijper & Feringa, *Angew. Chem. Int'l Ed.* 46:3693 (2007); Maeda et al., *J. Am. Chem. Soc'y* 128:7639 (2006); Sakurai et al., *J. Am. Chem. Soc'y* 128:5650 (2006); Canary et al., *Coord. Chem. Rev.* 254:2249 (2010)). In synthetic chemistry, interesting studies have included the employment of single enantiomer ligands with different solvents (Seerden et al., *Tetrahedron: Asymmetry* 6:1441 (1995); Seerden et al., *Tetrahedron Lett.* 35:4419 (1994); Seerden et al., *Tetrahedron* 53:11843 (1997); Sohtome et al., *Angew. Chem. Int'l Ed.* 49:9254 (2010)), counterions (Gothelf et al., *J. Org. Chem.* 61:346 (1996); Gothelf et al., *J. Org. Chem.* 63:5483 (1998); Crosignani et al., *Tetrahedron* 54:15721 (1998); Crosignani et al., *Tetrahedron Lett.* 40:7007 (1999); Desimoni et al., *Tetrahedron* 53:7671 (1997)), metals (Kinting et al., *J. Organomet. Chem.* 370:343 (1989); Ghosh et al., *Tetrahedron Lett.* 37:3815 (1996); Sibi et al., *J. Am. Chem. Soc'y* 120:6615 (1998); Yabu et al., *J. Am. Chem. Soc'y* 123: 9908 (2001)), and temperatures (Kanemasa et al., *J. Am. Chem. Soc'y* 121:8675 (1999)) in an attempt to toggle the enantioselectivity of a reaction, which has enjoyed varying degrees of success (Sibi & Liu, *Curr. Org. Chem.* 5:719 (2001); Zanoni et al., *Chem. Soc'y Rev.* 32:115 (2003); Penning & Jez, *Chem. Rev.* 101:3027 (2001); Tanaka & Hayashi, *Synthesis* 21:3361 (2008)). Most such systems reported to date have been discovered by serendipity, and rational design of catalysts with ready triggers to modulate or invert enantioselectivity have been elusive. A thiourea organocatalyst employing a phototriggered, helically chiral molecular rotor scaffold was recently designed (Wang & Feringa, *Science* 331:1429 (2011)). In this system, photoswitching produced thermally interconverting atropisomers that catalyzed the formation of enantiomeric products of the addition of a thiophenol to cyclohexenone. Redox-modulated catalysts have been reported that provide elements of allosteric reactivity control, but no redox-based system has been shown to control enantioselectivity (Slone et al., *J. Am. Chem. Soc'y* 119:10743 (1997); Gregson et al., *J. Am. Chem. Soc'y* 128:7410 (2006); Broderick et al., *Chem. Commun.* 47:9897 (2011); Broderick et al., *J. Am. Chem. Soc'y* 133:9278 (2011); Lorkovic et al., *J. Am. Chem. Soc'y* 117:3617 (1995)).

The field of asymmetric catalysis has been a boon towards the synthesis of chiral pharmaceuticals and chiral sensors. All asymmetric catalysts, though, are either directly synthesized from, or are enantiomerically resolved using, chiral natural products. Biological homochirality nearly always results in only one enantiomer or diastereomer in the biosynthetic pathway used to create chiral compounds, which leads to the scarce production of unnatural enantiomers. Predictably, this limits the availability of the catalysts that are derived from naturally disfavored chiral compounds that must be produced by often resource-intensive synthetic routes. The ability to toggle the enantioselectivity of a reaction by using a reconfigurable catalyst could conserve resources and reduce waste in asymmetric catalysis processes by eliminating the need to produce the enantiomer otherwise unavailable from nature's chiral pool.

The present invention is directed to overcoming these and other deficiencies in the art.

SUMMARY OF THE INVENTION

A first aspect of the present invention relates to a catalyst of Formula I:

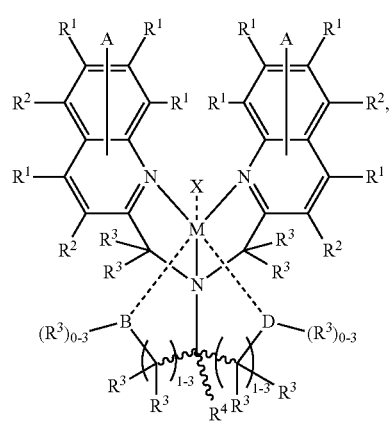

where:
  each $R^1$ is independently H; a lower alkyl; an aminyl; —$OR^6$ where $R^6$ is hydrogen or a lower alkyl; or the attachment point for A;
  each $R^2$ is independently H; a lower alkyl; an aminyl; or —$OR^6$ where $R^6$ is hydrogen or a lower alkyl;
  each $R^3$ and $R^4$ is independently hydrogen; an alkyl; an alkenyl; an alkynyl; an aminyl; a carbonyl; a cycloalkyl; a heterocyclyl; an aryl; a heteroaryl; an arylalkyl; an acyl; —$OR^5$ where $R^5$ is hydrogen, an alkyl, an alkenyl, an alkynyl, a cycloalkyl, a heterocyclyl, an aryl, a heteroaryl, an arylalkyl, or an acyl; or —$(CH_2)_{0-1}N(R^5)_2$ where each $R^5$ is independently hydrogen, an alkyl, an alkenyl, an alkynyl, a cycloalkyl, a heterocyclyl, an aryl, a heteroaryl, an arylalkyl, or an acyl;
  each A is a catalytic moiety;
  B and D are atoms having different ionization potentials;
  M is a metal;
  X is absent, a solvent, or a counterion;
  each ⁓ is a bond of undefined stereochemistry; and
  each - - - - is an optional bond with the proviso that:
    (i) the bond between M and B present and the bond between M and D is absent; or
    (ii) the bond between M and B is absent and the bond between M and D is present.

The present invention is further directed to catalysts of Formula I' and Formula I", and the enantiomers thereof:

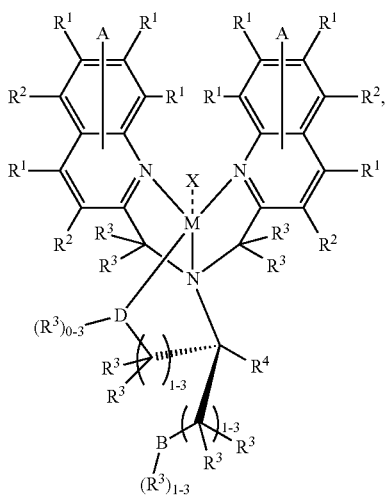

I'

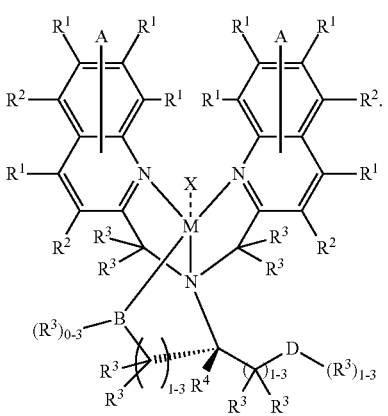

I"

A second aspect of the present invention relates to a method of producing a compound having a stereocenter, the method comprising: reacting a starting compound in the presence of a catalyst of the present invention under conditions effective to produce the compound having a stereocenter.

A third aspect of the present invention relates to a method of producing a compound having at least two stereocenters, the method comprising: (i) reacting a starting compound in the presence of a first catalyst under conditions effective to produce a first product compound, the first product compound having at least one stereocenter; and (ii) reacting the first product compound or a subsequent reaction product thereof in the presence of a second catalyst under conditions effective to produce a second product compound, the second product compound having at least two stereocenters; where the first catalyst and the second catalyst are each independently a catalyst of Formula I' (or enantiomer thereof) or a catalyst of Formula I" (or enantiomer thereof).

The catalysts of the present invention catalyze enantioselective reactions. Either enantiomer of the product can be predetermined by selection of the configuration of the metal complex. By way of example, copper-based catalysts of the present invention have been shown to catalyze, e.g., the enantioselective addition of diethyl malonate to trans-β-nitrostyrene. Either enantiomer of the product can be predetermined by selection of the oxidation state of the copper ion. Enantiomeric excesses of up to 72% (S) and 70% (R) were obtained in acetonitrile. The ability of the catalyst to invert enantiomeric preference was reproduced with several different solvents and bases. Facile interconversion between the $Cu^{2+}$ and $Cu^+$ redox states allowed easy access to both active helical forms of the complex, and therefore dial-in enantioselectivity. Malonate substrates that include a prochiral center were also evaluated. The enantioselectivity of the Michael addition product can still be reversed depending on the oxidation state of the catalyst.

The metal ion is not involved in the reaction; it only serves to reconfigure the organic ligand to approximate enantiomeric geometry. Thus, catalysts of the present invention can employ other metals in place of copper. Such catalysts will not necessarily be redox-reversible, but may nevertheless be useful for catalyzing enantioselective reactions, including those producing unnatural enantiomers that may otherwise be difficult to obtain.

BRIEF DESCRIPTION OF THE DRAWINGS

FIG. 8 is the $^1$H-NMR spectra of aldehyde 7.

FIGS. 11A-B are the $^1$H-NMR (FIG. 11A) and $^{13}$C-NMR (FIG. 11B) spectra of (S)-4.

FIGS. 12A-C are the HPLC chromatographs for 4 (racemic) (FIG. 12A), (S)-4 (FIG. 12B), and (R)-4 (FIG. 12C).

DETAILED DESCRIPTION OF THE INVENTION

A first aspect of the present invention relates to a catalyst of Formula I:

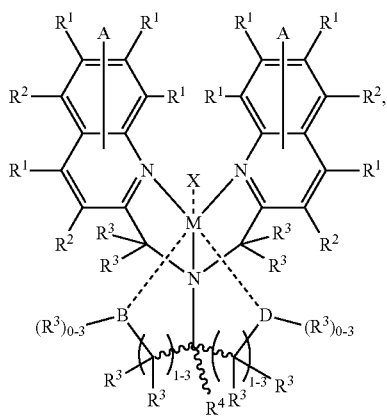

where:
- each $R^1$ is independently H; a lower alkyl; an aminyl; —$OR^6$ where $R^6$ is hydrogen or a lower alkyl; or the attachment point for A;
- each $R^2$ is independently H; a lower alkyl; an aminyl; or —$OR^6$ where $R^6$ is hydrogen or a lower alkyl;
- each $R^3$ and $R^4$ is independently hydrogen; an alkyl; an alkenyl; an alkynyl; an aminyl; a carbonyl; a cycloalkyl; a heterocyclyl; an aryl; a heteroaryl; an arylalkyl; an acyl; —$OR^5$ where $R^5$ is hydrogen, an alkyl, an alkenyl, an alkynyl, a cycloalkyl, a heterocyclyl, an aryl, a heteroaryl, an arylalkyl, or an acyl; or —$(CH_2)_{0-1}N(R^5)_2$ where each $R^5$ is independently hydrogen, an alkyl, an alkenyl, an alkynyl, a cycloalkyl, a heterocyclyl, an aryl, a heteroaryl, an arylalkyl, or an acyl;
- each A is a catalytic moiety;
- B and D are atoms having different ionization potentials;
- M is a metal;
- X is absent, a solvent, or a counterion;
- each ～～ is a bond of undefined stereochemistry; and
- each - - - - is an optional bond with the proviso that:
  - (i) the bond between M and B present and the bond between M and D is absent; or
  - (ii) the bond between M and B is absent and the bond between M and D is present.

The catalysts of the present invention are catalysts (including redox-reconfigurable catalysts) derived from L-methionine and incorporating catalytic groups. These metal complexes catalyze enantioselective reactions. Either enantiomer of the product can be predetermined by selection of the configuration of the metal complex. By way of example, copper-based catalysts of the present invention can be used to predetermine the enantiomer of the product by selecting the oxidation state of the copper ion. Facile interconversion between the $Cu^{2+}$ and $Cu^+$ redox states, as depicted below, allows easy access to both active helical forms of the complex, and therefore dial-in enantioselectivity.

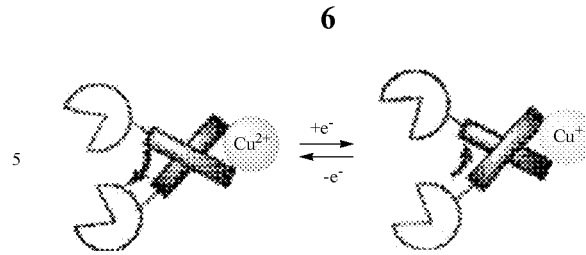

Figure 1:
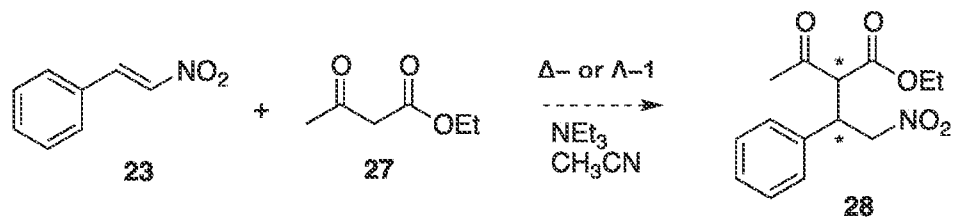
FIG. 1 is a schematic illustration of the addition of prochiral compound 27 to nitrostyrene 26 using catalyst Δ/Λ-1.

The generation of another stereocenter to form diastereomeric (and polystereomeric) products can also be achieved using catalysts of the present invention. By way of example, diastereomers could be formed via conjugate addition reactions by either adding a substituent onto a nitroalkene or by using prochiral 1,3-dicarbonyl nucleophiles, such as $CH_3$—C(=O)—$CH_2$—C(=O)—OEt, MeO—C(=O)—$CH_2$—C(=O)—Ot-Bu, BzO—C(=O)—$CH_2$—C(=O)—OEt, EtO—C(=O)—$CH_2$—C(=O)—Ot-Bu, and BzO—C(=O)—$CH_2$—C(=O)—Ot-Bu, with nitrostyrene (see, for example, FIG. 1 and Table 6) (Okino et al., "Enantio- and Diastereoselective Michael Reaction of 1,3-Dicarbonyl Compounds to Nitroolefins Catalyzed by a Bifunctional Thiourea," J. Am. Chem. Soc'y 127:119-25 (2005); Huang & Jacobsen, "Highly Enantioselective Direct Conjugate Addition of Ketones to Nitroalkenes Promoted by a Chiral Primary Amine-Thiourea Catalyst," J. Am. Chem. Soc'y 128:7170-01 (2006); Zhang et al., J. Catalysis 265:155-60 (2009), which are hereby incorporated by reference in their entirety). The mechanism of addition of these prochiral compounds should be very similar to the conjugate additions described in the Examples herein.

Figure 2:
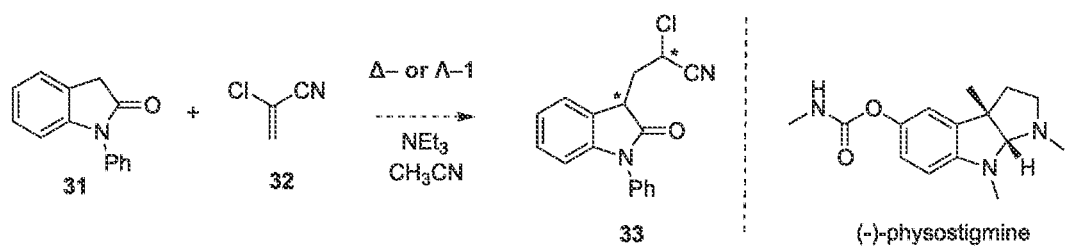
FIG. 2 is a schematic illustration of the asymmetric addition of oxindole 31 to 2-chloroacrylonitrile using catalyst Δ/Λ-1.

It is expected that other conjugate addition reactions can also be catalyzed besides additions to nitroalkenes. There exists a wide array of electrophiles for Michael additions. Additionally, many of those same electrophilic compounds have been used as reactants in enantioselective conjugate addition reactions using (thio)urea catalysts. Important motifs such as chiral N-alkylated piperidinols (Uehara et al., "Organocatalytic Asymmetric Assembly Reactions for the Syntheses of Carbohydrate Derivatives by Intermolecular Michael-Henry Reactions," Proc. Nat'l Acad. Sci. USA 107: 20672-77 (2010); Imashiro et al., "One-Pot Enantioselective Syntheses of Iminosugar Derivatives Using Organocatalytic Anti-Michael-Anti-Aza-Henry Reactions," Org. Lett. 12:5250-53 (2010), which are hereby incorporated by reference in their entirety), carbazolespirooxindole skeletons (Tan et al., "Highly Efficient Hydrogen-Bonding Catalysis of the Diels-Alder Reaction of 3-Vinylindoles and Methyleneindolinones Provides Carbazolespirooxindole Skeletons," J. Am. Chem. Soc'y 133:12354-57 (2011); Tan et al., "Construction of Bispirooxindoles Containing Three Quaternary Stereocentres in a Cascade Using a Single Multifunctional Organocatalyst," Nat. Chem. 3:473-77 (2011), which are hereby incorporated by reference in their entirety), and unnatural amino acids have been obtained using (thio)urea based catalysts (Zuend et al., "Scaleable Catalytic Asymmetric Strecker Syntheses of Unnatural α-Amino Acids," Nature 461:968-70 (2009), which is hereby incorporated by reference in its entirety). It is expected that (thio)urea catalysts of the present invention should also be effective for many kinds of related conjugate additions (for example, the addition of oxindole 31 to 2-chloroacrylonitrile (see FIG. 2) and behave in a similar asymmetric (and, in the case of reversible catalysts, ambidextrous) fashion. Similar reactions to synthesize skeletal scaffolds of oxindole alkaloids such as physostigmine, asperazine, and horsfiline have been studied (Li et al., "Asymmetric Conjugate Addition of Oxindoles to 2-Chloroacrylonitrile: A Highly Effective Organocatalytic Strategy for Simultaneous Construction of 1,3-Nonadjacent Stereocenters Leading to Chiral Pyrroloindolines," *Chemistry* 16:14290-94 (2010); Li et al., "Physical Organic Study of Structure-Activity-Enantioselectivity Relationships in Asymmetric Bifunctional Thiourea Catalysis: Hints for the Design of New Organocatalysts," *Chemistry* 16:450-55 (2010), which are hereby incorporated by reference in their entirety). The present catalysts could bring about the ability to access different enantiomers (or diastereomers) of these addition products. The significance of selectively obtaining different stereoisomers of alkaloids can be seen when discussing the biological activity of physostigmine (Ashimori et al., "Catalytic Asymmetric Synthesis of Either Enantiomer of Physostigmine. Formation of Quaternary Carbon Centers with High Enantioselection by Intramolecular Heck Reactions of (Z)-2-Butenanilides," *J. Org. Chem.* 58:6949-51 (1993); Takano & Ogasawara, "Alkaloids of the Calabar Bean," *Alkaloids* 36:225-51 (1989); Brossi, "Bioactive Alkaloids. 4. Results of Recent Investigations with Colchicine and Physostigmine," *J. Med. Chem.* 33:231 (1990), which are hereby incorporated by reference in their entirety). Only (−)-physostigmine is an acetylcholinesterase inhibitor that is used for treating diseases such as glaucoma. (+)-Physostigmine lacks the same biological effectiveness (Canary, "Redox-Triggered Chiroptical Molecular Switches," *Chem. Soc'y Rev.* 38:747-56 (2009), which is hereby incorporated by reference in its entirety). Thus, the ability to stereoselect between different oxindole products could be of great benefit in the search of biologically active scaffolds.

Asymmetric thiourea catalysts have been able to carry out a much broader range of reactions than just conjugate addition reactions (Connon, "The Design of Novel, Synthetically Useful (Thio)Urea-Based Organocatalysts," *Synlett* 2009:354-76 (2009), which is hereby incorporated by reference in its entirety), such as asymmetric aldol and Diels-alder reactions (Connon, "Organocatalysis Mediated by (Thio) Urea Derivatives," *Chemistry* 12:5418-27 (2006), which is hereby incorporated by reference in its entirety). Work using chiral auxiliaries has proven to be a powerful method for the synthesis of asymmetric aldol products (Evans et al., "Enantioselective Aldol Condensations. 2. Erythro-Selective Chiral Aldol Condensations via Boron Enolates," *J. Am. Chem. Soc'y* 103:2127-29 (1981); Ager et al., "1,2-Amino Alcohols and Their Heterocyclic Derivatives as Chiral Auxiliaries in Asymmetric Synthesis," *Chem. Rev.* 96:835-76 (1996); Velazquez & Olivo, "The Application of Chiral Oxazolidinethiones and Thiazolidinethiones in Asymmetric Synthesis," *Curr. Org. Chem.* 6:303 (2002), which are hereby incorporated by reference in their entirety). Although these auxiliaries have high utility there are some shortcomings regarding stereoselectivity: it is known that when performing an aldol reaction with an N-acyloxazolidinone, the diastereoselectivity of the aldol adducts is typically low (Evans et al., "Enantioselective Aldol Condensations. 2. Erythro-Selective Chiral Aldol Condensations Via Boron Enolates," *J. Am. Chem. Soc'y* 103:2127-29 (1981), which is hereby incorporated by reference in its entirety). Some solutions exist for obtaining higher diastereoselectivity, but these require multiple steps and stoichiometric amounts of auxiliary (Hodge & Olivo, "Stereoselective Aldol Additions of Titanium Enolates of N-Acetyl-4-Isopropyl-Thiazolidinethione," *Tetrahedron* 60:9397-403 (2004), which is hereby incorporated by reference in its entirety). Alternatively, proline catalyzed asymmetric aldol reactions have been useful, but nearly all such catalysts are designed using the naturally occurring L-proline (Notz et al., "Enamine-Based Organocatalysis With Proline and Diamines: The Development of Direct Catalytic Asymmetric Aldol, Mannich, Michael, and Diels-Alder Reactions," *Acc. Chem. Res.* 37:580-91 (2004), which is hereby incorporated by reference in its entirety). (Thio)urea catalysts of the present invention provide useful alternative. By way of example, it is expected that (thio)urea catalysts of the present invention such as, e.g., Δ/Λ-1 can be used to catalyze asymmetric aldol reactions with N-acyloxazolidinones. These types of oxazolidinones have been shown to bind to thiourea groups to catalyze asymmetric conjugate addition reactions (Inokuma et al., "Thiourea-Catalyzed Asymmetric Michael Addition of Activated Methylene Compounds to α,β-Unsaturated Imides: Dual Activation of Imide by Intra- and Intermolecular Hydrogen Bonding," *J. Am. Chem. Soc'y* 128: 9413-19 (2006), which is hereby incorporated by reference in its entirety). The urea moieties of ambidextrous catalyst Δ/Λ-1 should behave in the same manner. The use of catalytic amounts of base should activate the aldol reaction.

Figure 3:
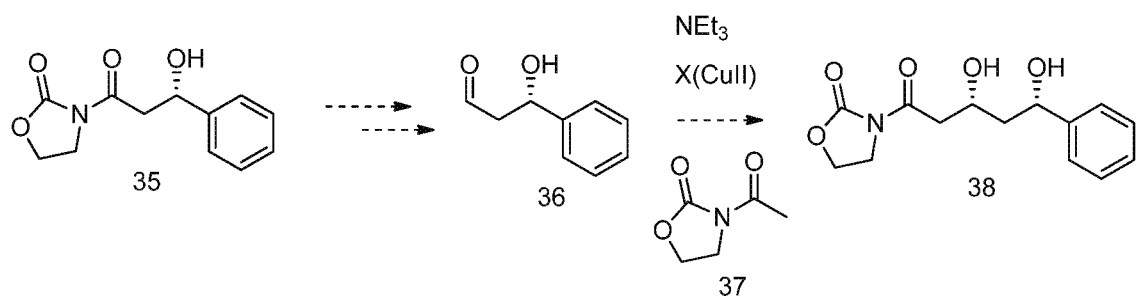
FIG. 3 is a schematic illustration of an example of iterative aldol strategy which could be used to construct asymmetric polyol motifs.

Iterative asymmetric aldol reactions, as shown in FIG. 3, are also contemplated. These reactions could unlock the potential ability to selectively obtain any desired stereoisomer of a polyol. Several polyketide natural products feature various asymmetric polyol motifs (Evans et al., "Total Synthesis of the Macrolide Antibiotic Rutamycin B," *J. Am. Chem. Soc'y* 115:11446-59 (1993), which is hereby incorporated by reference in its entirety). Creating an iterative process to obtain these motifs would greatly simplify the synthesis of many polyketides.

Figure 4:
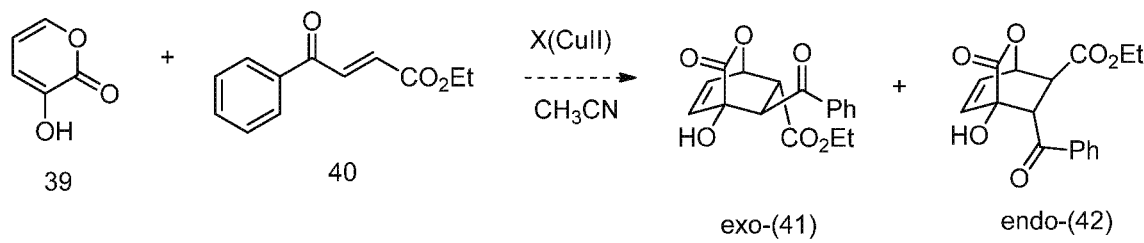
FIG. 4 is a schematic illustration of the urea catalyzed Diels-Alder reaction using ambidextrous catalyst Δ/Λ-1.

Another suitable reaction according to the present invention is the asymmetric Diels-Alder cycloaddition. This is another transformation in which thio(urea) catalysis has proven to be effective (Wittkopp & Schreiner, "Metal-Free, Noncovalent Catalysis of Diels-Alder Reactions by Neutral Hydrogen Bond Donors in Organic Solvents and in Water," *Chemistry* 9:407-14 (2003); Schreiner & Wittkopp, "H-Bonding Additives Act Like Lewis Acid Catalysts," *Org. Lett.* 4:217-20 (2002); Mori et al., "Efficient Organocatalytic Hetero-Diels-Alder Reactions of Activated Ketones Under High Pressure for Direct Access to δ-Lactones," *Synlett* 2009 (14):2346-50 (2009), which are hereby incorporated by reference in their entirety). It has been shown that complex carbazolespirooxindole skeletons can be quickly synthesized by a bisthiourea catalyzed Diels-Alder reaction (Tan et al., "Highly Efficient Hydrogen-Bonding Catalysis of the Diels-Alder Reaction of 3-Vinylindoles and Methyleneindolinones Provides Carbazolespirooxindole Skeletons," *J. Am. Chem. Soc'y* 133:12354-57 (2011), which is hereby incorporated by reference in its entirety). A simpler model reaction involving thiourea catalyzed Diels-Alder reactions of 2-pyrones has also been described (Wang et al., "Asymmetric Diels-Alder Reactions of 2-Pyrones With a Bifunctional Organic Catalyst," *J. Am. Chem. Soc'y* 129:6364-65 (2007), which is hereby incorporated by reference in its entirety). The use of Diels-Alder reactions involving 2-pyrones in natural product synthesis has been established and creating an asymmetric method for obtaining either enantiomer of a Diels-Alder adduct would be particularly useful (Corey & Kozikowski, "3-Hydroxy-2-Pyrone as a Vinylketene Equivalent for the Synthesis of Dmydrophenols and Cyclohexanones," *Tetrahedron Lett.* 2369-92 (1975); Baran & Burns, "Total Synthesis of (±)-Haouamine A," *J. Am. Chem. Soc'y* 128:3908-09 (2006), which are hereby incorporated by reference in their entirety). It is expected that (thio)urea catalysts of the present invention such as, e.g., Δ/Λ-1 can be used to catalyze asymmetric Diels-Alder reactions as well, as shown in FIG. 4 (2-pyrone 39 and enone 40 as reactants are shown by way of example).

As used herein, the term "alkyl" means an aliphatic hydrocarbon group which may be straight or branched having about 1 to about 6 carbon atoms in the chain. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Exemplary alkynyl groups include ethynyl, propynyl, n-butynyl, 2-butynyl, 3-methylbutynyl, and n-pentynyl.

As used herein, the term "aminyl" refers to a moiety of formula $-NR_2$ or $-N^+R_3$, where each R is independently hydrogen, an alkyl, an alkenyl, an alkynyl, a carbonyl, or a sulfonyl appendage.

As used herein, the term "cycloalkyl" refers to a non-aromatic saturated or unsaturated mono- or polycyclic ring system which may contain 3 to 6 carbon atoms, and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

As used herein, the term "heterocyclyl" refers to a stable 3- to 18-membered ring system that consists of carbon atoms and from one to five heteroatoms selected from the group consisting of nitrogen, oxygen, and sulfur. The heterocyclyl may be a monocyclic or a polycyclic ring system, which may include fused, bridged, or spiro ring systems; and the nitrogen, carbon, or sulfur atoms in the heterocyclyl may be optionally oxidized; the nitrogen atom may be optionally quaternized; and the ring may be partially or fully saturated. Representative monocyclic heterocyclyls include piperidine, piperazine, pyrimidine, morpholine, thiomorpholine, pyrrolidine, tetrahydrofuran, pyran, tetrahydropyran, oxetane, and the like. Representative polycyclic heterocyclyls include indole, isoindole, indolizine, quinoline, isoquinoline, purine, carbazole, dibenzofuran, chromene, xanthene, and the like.

As used herein, the term "aryl" refers to an aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

As used herein, "heteroaryl" refers to an aromatic ring system that consists of carbon atoms and from one to five heteroatoms selected from the group consisting of nitrogen, oxygen, and sulfur. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl.

The term "arylalkyl" refers to a moiety of the formula $-R^aR^b$ where $R^a$ is an alkyl or cycloalkyl as defined above and $R^b$ is an aryl or heteroaryl as defined above.

As used herein, the term "acyl" means a moiety of formula R— carbonyl, where R is an alkyl, cycloalkyl, aryl, or heteroaryl as defined above. Exemplary acyl groups include formyl, acetyl, propanoyl, benzoyl, and propenyl.

As used herein, a "catalytic moiety" is a moiety capable of catalyzing a given reaction. Suitable catalytic moieties include, for example, (thio)ureas; guanidines, amides, phenols, carboxylic acids, and other hydrogen bond donating groups; and a moiety of formula $-E^1-NH-C(=G)-NH-E^2$, where $E^1$ and $E^2$ are each independently absent, an alkyl, an aryl, or a heteroaryl; and G is O, S, NR, or $-N^+R_2$, where each R is independently hydrogen, an alkyl, an alkenyl, an alkynyl, an aminyl, a carbonyl, a cycloalkyl, a heterocyclyl, an aryl, a heteroaryl, an arylalkyl, or an acyl. In at least one preferred embodiment, the catalytic moiety is a moiety of formula $-E^1-NH-C(=G)-NH-E^2$. The catalytic moieties may be the same or different.

Figure 5:
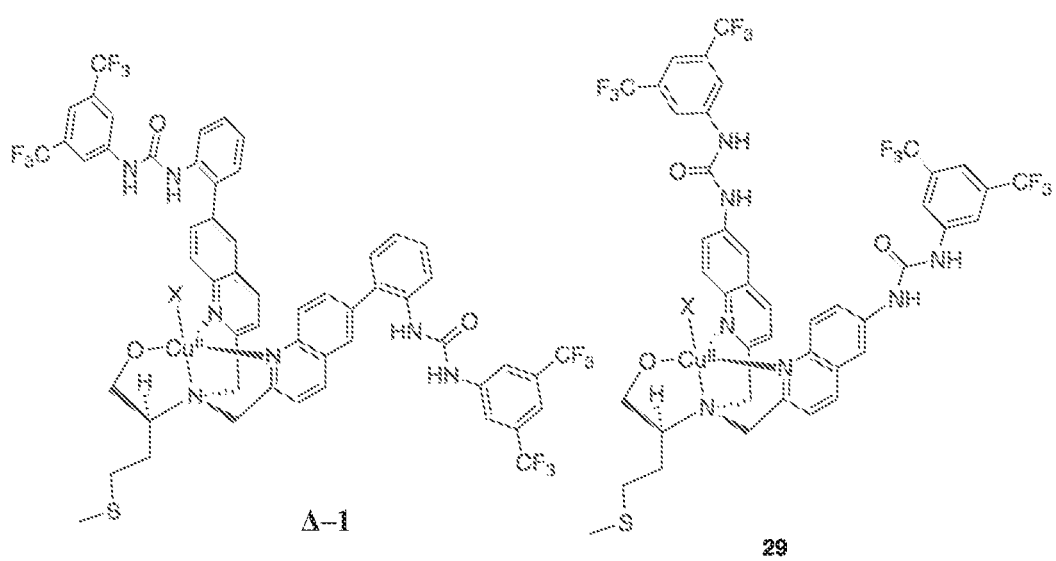
FIG. 5 is a comparison of exemplary catalyst Δ-1 with 29, which orients the ureas away from the basal plane of the $Cu^{2+}$ inner coordination sphere.

The catalysts described in the Examples herein contain a catalytic moiety featuring an aryl (e.g., phenyl group) connecting the reactive portion of the catalytic moiety (e.g., a urea) to the quinoline moiety in an ortho position. By way of example, the reactive portion (e.g., urea group) could be projected further away from the quinoline scaffold by altering the attachment point of A. The reactive portion (e.g., urea group) could also be directly attached to the quinoline group without the ortho-aryl linker, in which case the reactive portion (e.g., urea group) would project orthogonal to their orientation in the current catalyst design, as shown in FIG. 5.

B and D are atoms having different ionization potentials. Preferably, the difference is at least about 50 kJ/mol, at least about 100 kJ/mol, or at least about 150 kJ/mol. When M is copper, B and D preferably have different ionization potentials such that oxidizing the metal results in the formation of a bond between the metal and D, while reducing the metal results in the formation of a bond between the metal and B. In at least one embodiment, B is oxygen, sulfur, or selenium. In at least one embodiment, D is oxygen, sulfur, or selenium. In at least one embodiment, one of B and D is oxygen and the other is sulfur or selenium.

Suitable metals according to this and all aspects of the present invention include, for example, Cu(I), Cu(II), Ag(I), Hg(II), Ni(II), Cd(II), Zn(II), Fe(II/III), and Co(II), and other first row transition metals of oxidation state II or higher. In a preferred embodiment, the metal is one that is capable of having two oxidation states, e.g., copper. Although copper was used in the Examples herein, as will be apparent to the skilled artisan, other metals can be used in place of Cu(I) and Cu(II) in the catalysts of the present invention. Metals that act like Cu(I) include Ag(I), Hg(II), Ni(II), and Cd(II), while many metals may act like Cu(II), notably Zn(II), Fe(II/III), Co(II), and other first row transition metals of oxidation state II or higher (Holmes et al., "Stereodynamic Coordination Complexes. Dependence of Exciton Coupled Circular Dichroism Spectra on Molecular Conformation and Shape," *Monatsh. Chem.* 136:461-75 (2005); Das et al., "Exploring the Scope of Redox-Triggered Chiroptical Switches: Syntheses, X-Ray Structures and Circular Dichroism of Cobalt and Nickel Complexes of N,N-Bis(arylmethyl)methionine Derivatives," *Chirality* 20:585-89 (2008), which are hereby incorporated by reference in their entirety).

As noted above "X" in the catalysts of the present invention is absent, a solvent, or a counterion. The solvent can be any solvent in which the catalyst is dissolved. Solvents are well known in the art. A "counterion" as used herein refers to the species in solution complementary in charge to the catalyst. Suitable counterions include, for example, halide, nitrate, sulfate, sulfonate, perchlorate, hexafluorophosphate, hexafluoroantimonate, and tetraarylborate.

Suitable catalysts according to this and all aspects of the present invention include, without limitation, those of Formula I' and Formula I", and the enantiomers thereof:

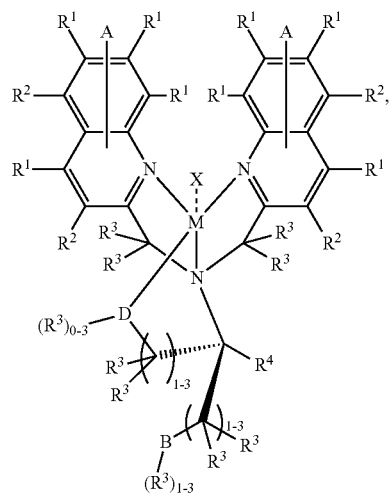

I'

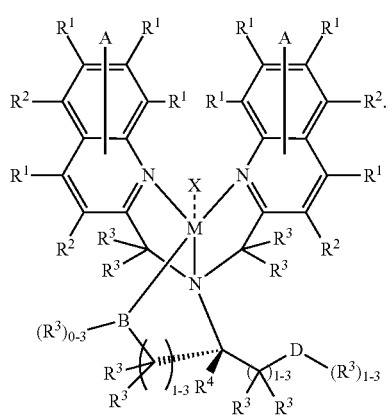

I"

(In all aspects of the present invention, an "enantiomer" of a catalyst of the present invention refers to a catalyst with the opposite stereochemistry as that of the reference catalyst at the carbon to which $R^4$ is attached, without regard to any other asymmetric atom that may be present.) As will be apparent to the skilled artisan, catalysts of Formula I' and the enantiomers of catalysts of Formula I" are "right-handed" catalysts, while catalysts of Formula I" and the enantiomers of catalysts of Formula I' are "left-handed" catalysts.

In a preferred embodiment, the catalyst is a catalyst of Formula IA:

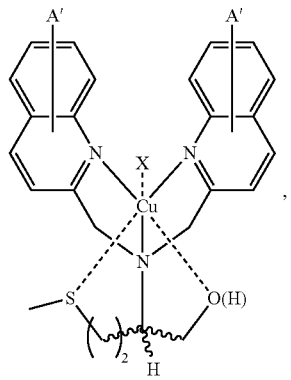

IA where each A' is independently a moiety of formula -$E^1$-NH—C(=O)—NH-$E^2$, where $E^1$ is an aryl or a heteroaryl and $E^2$ is an alkyl, an aryl, or a heteroaryl. Suitable examples of catalysts of Formula IA include, for example, those of Formula IB (e.g., Λ-1) and Formula IC (e.g., Δ-1), and the enantiomers thereof:

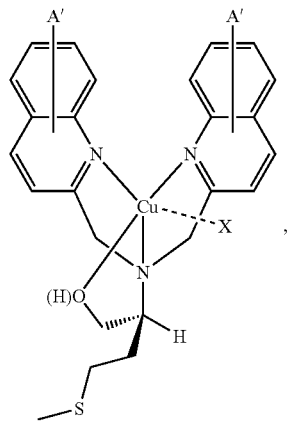

IB

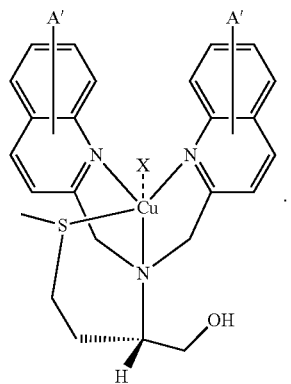

IC

The catalysts of the present invention may be made using standard methods that will be apparent to the skilled artisan. Such methods include those described in Examples 1-4 herein. Catalysts of Formula I' and I" (and the enantiomers thereof) in which the metal has two oxidation states can also be made, respectively, by oxidizing the corresponding catalyst of Formula I" (or enantiomer thereof) and by reducing the corresponding catalyst of Formula I' (or enantiomer thereof).

Another aspect of the present invention relates to a method of producing a compound having a stereocenter. This method involves reacting a starting compound in the presence of a catalyst of the present invention under conditions effective to produce the compound having a stereocenter. As will be apparent to the skilled artisan, this method may also be used to add one or more stereocenters to a starting compound that already contains one or more stereocenters.

Reacting according to this aspect of the present invention preferably involves carrying out a reaction selected from the group consisting of conjugate addition reactions, aldol reactions, and Diels-Alder reactions. In a preferred embodiment, the reaction is a Michael addition reaction, including that of the type illustrated below.

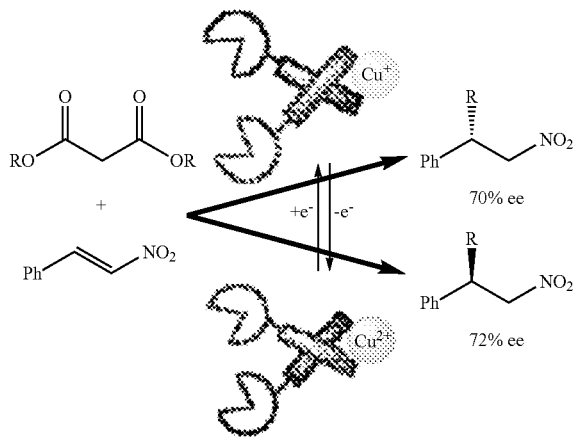

In at least one embodiment of this aspect of the present invention, the product compound is one that can exist as one of two enantiomers. In such instances, a catalyst of the present invention can be selected to preferentially produce one of the enantiomers over the other enantiomer. For example, right-handed catalysts of the present invention can be used to preferentially produce one enantiomer of the product of a reaction, and the corresponding left-handed catalysts of the present invention can be used to preferentially produce the other product enantiomer. (Typically, when the metal is copper, right-handed catalysts will preferentially produce the (S)-enantiomer and left-handed catalysts will preferentially produce the (R)-enantiomer.)

At least one embodiment of this aspect of the present invention involves the catalysis in a solution of two reactions that occur simultaneously but in which the stereochemical of each reaction (producing products "P1" and "P2") is controlled by the same catalyst. Thus, depending on the starting state of the catalyst and the timing of the switch of the catalyst to its alternate form, the outcome of the reaction may be to produce (S)-P1 and (S)-P2, (S)-P1 and (R)-P2, (R)-P1 and (S)-P2, or (R)-P1 and (R)-P2.

Another aspect of the present invention relates to a method of producing a compound having at least two stereocenters. This method involves reacting a starting compound in the presence of a first catalyst under conditions effective to produce a first product compound, the first product compound having at least one stereocenter. The first product compound or a subsequent reaction product thereof is reacted in the presence of a second catalyst under conditions effective to produce a second product compound, the second product compound having at least two stereocenters. The first catalyst and the second catalyst are each independently a catalyst of Formula I' or enantiomer thereof, or a catalyst of Formula I" or enantiomer thereof.

As will be apparent to the skilled artisan, by selecting from catalysts of Formula I' and/or Formula I", and their enantiomers, the present method may be used to produce compounds having all (S)-stereocenters or all (R)-stereocenters, as well as compounds having a mixture of the two. When the metal is copper and at least one catalyst of Formula I' (or enantiomer thereof) is used and at least one corresponding catalyst of Formula I" (or enantiomer thereof) is used, one of the catalysts can optionally be produced in situ by adding an oxidizing or reducing agent at an appropriate stage in the reaction, as will be apparent to the skilled artisan.

In at least one embodiment, the method may involve (i) reacting the starting compound in the presence of the first catalyst under conditions effective to produce the first product compound, (ii) reacting the first product compound in the presence of the second catalyst under conditions effective to produce a second product compound, the second product compound comprising at least two stereocenters, (iii) optionally reacting the product of the immediately previous reacting step in the presence of an additional catalyst of Formula I' (or enantiomer thereof) or Formula I" (or enantiomer thereof) under conditions effective to produce a product compound comprising an additional stereocenter, and (iv) optionally repeating step (iii) one or more times to produce a compound having multiple stereocenters.

In all aspects of the present invention relating to methods of producing compounds using one or more catalysts of the present invention, methods that include other reaction steps, which are not carried out in the presence of a catalyst of the present invention, are also contemplated.

The present invention may be further illustrated by reference to the following examples.

EXAMPLES

The following Examples are intended to illustrate, but by no means are intended to limit, the scope of the present invention as set forth in the appended claims.

Example 1

General Information

All commercial materials were purchased without further purification. Small-scale reactions were carried out in 20 mL Fisher Scientific disposable scintillation vials. Other reactions were carried out using oven-dried (160° C.) glassware. Solvents were purchased from Aldrich with Sure-Seal bottles. $^1$H-NMR and $^{13}$C-NMR were obtained using a Bruker AC 400 (400 MHz) NMR. $^{13}$C-NMR were obtained at 100 MHz on the same NMR. All chemical shifts are reported in parts per million (ppm) with reference to solvent residual peaks. The ESI mass spectra were obtained with an Agilent 1100 Series Capillary LCMSD Trap XCT Spectrometer using acetonitrile solutions of the products. Circular dichroism spectra were acquired with an AVIV Model 202SF CD spectroscope. Enantiomeric excess was determined on an Agilent 1200 series HPLC with Daicel Chemical Industries, LTD. Chiralpak OD (0.46 cm×25 cm) column.

Example 2

Synthesis of Catalyst Ligand

The catalyst ligand was synthesized as shown in Scheme 1 below.

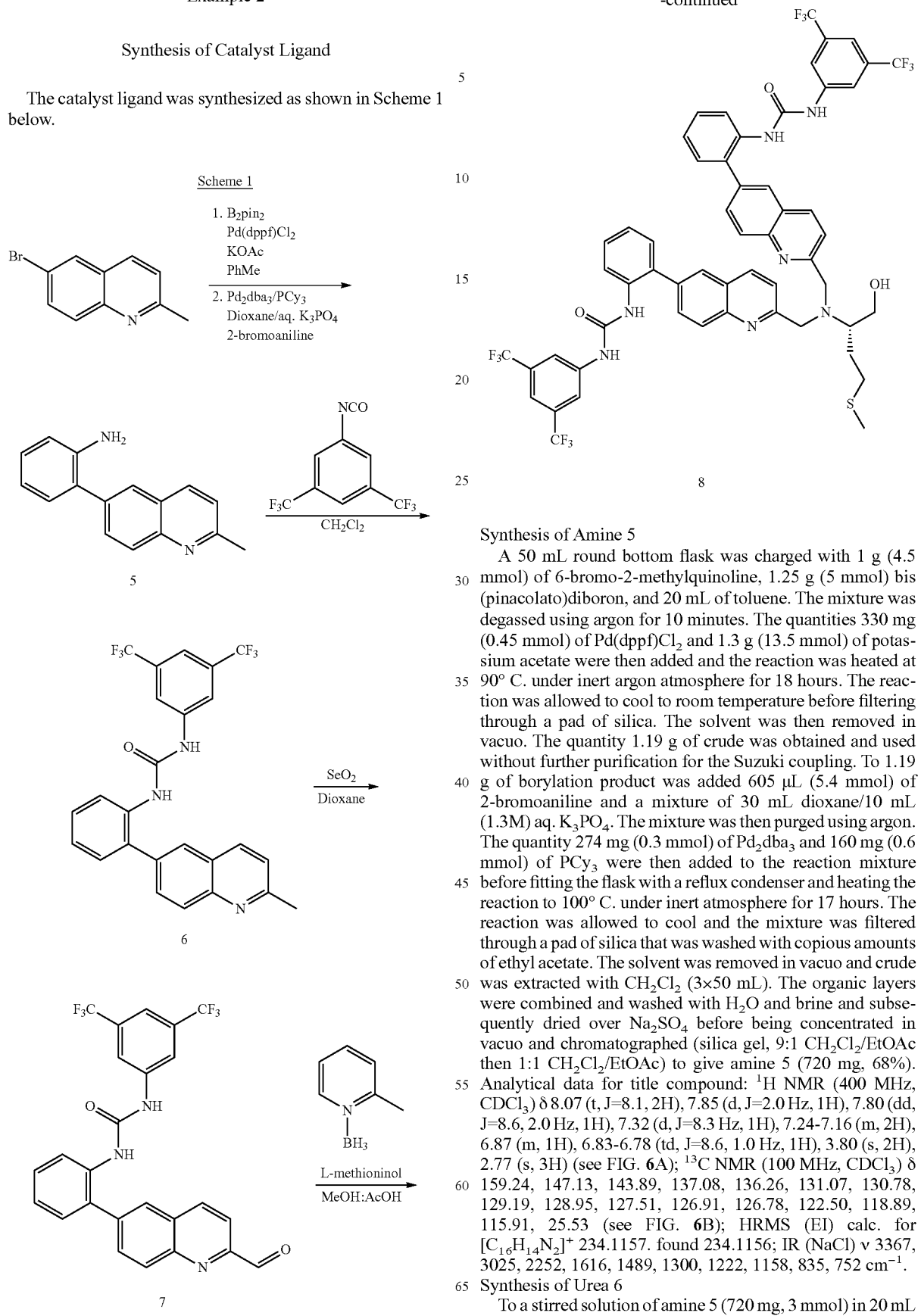

Synthesis of Amine 5

Figure 6:
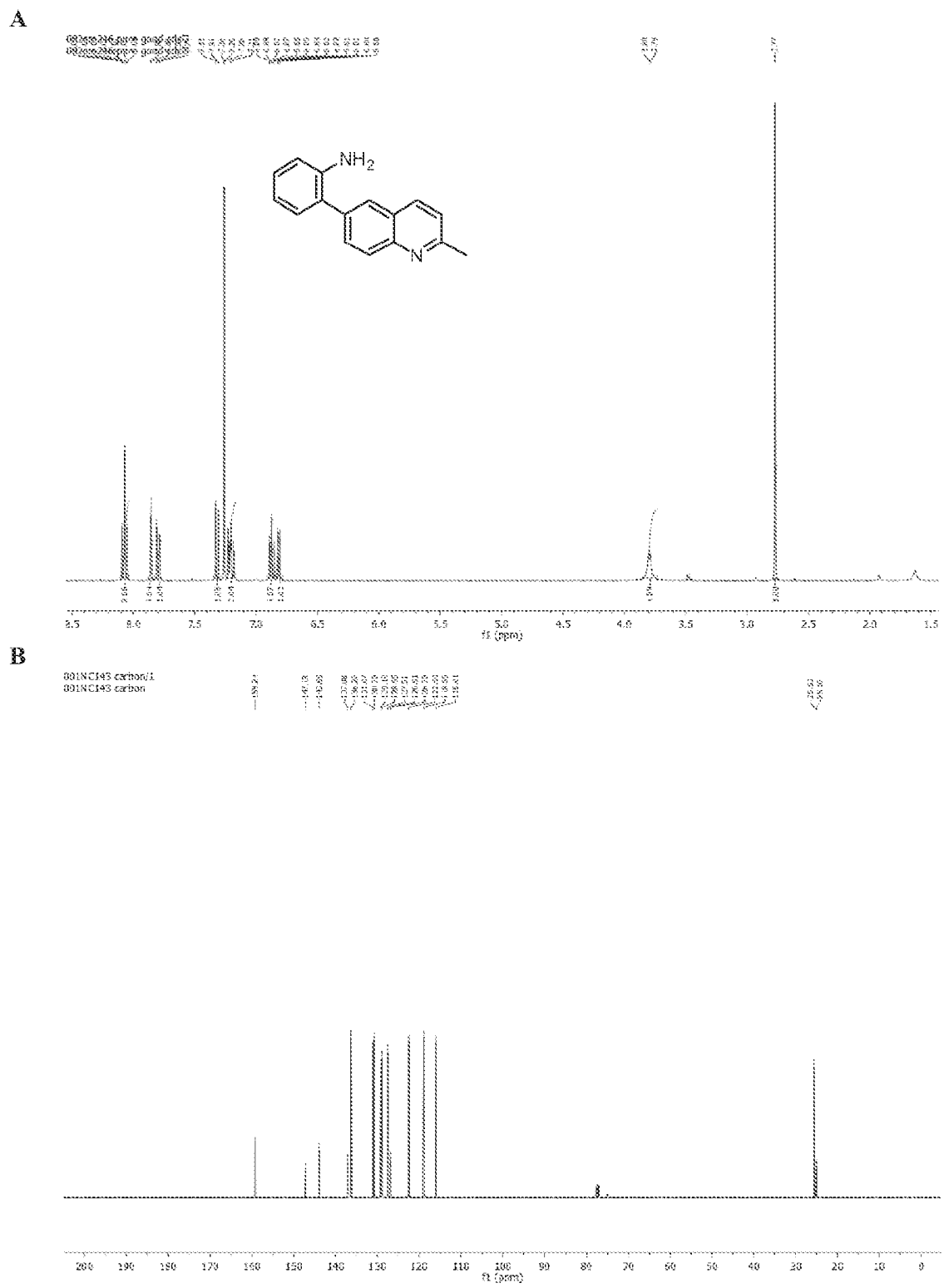
FIGS. 6A-B are the $^1$H-NMR (FIG. 6A) and $^{13}$C-NMR (FIG. 6B) spectra of amine 5.

A 50 mL round bottom flask was charged with 1 g (4.5 mmol) of 6-bromo-2-methylquinoline, 1.25 g (5 mmol) bis(pinacolato)diboron, and 20 mL of toluene. The mixture was degassed using argon for 10 minutes. The quantities 330 mg (0.45 mmol) of Pd(dppf)Cl$_2$ and 1.3 g (13.5 mmol) of potassium acetate were then added and the reaction was heated at 90° C. under inert argon atmosphere for 18 hours. The reaction was allowed to cool to room temperature before filtering through a pad of silica. The solvent was then removed in vacuo. The quantity 1.19 g of crude was obtained and used without further purification for the Suzuki coupling. To 1.19 g of borylation product was added 605 μL (5.4 mmol) of 2-bromoaniline and a mixture of 30 mL dioxane/10 mL (1.3M) aq. K$_3$PO$_4$. The mixture was then purged using argon. The quantity 274 mg (0.3 mmol) of Pd$_2$dba$_3$ and 160 mg (0.6 mmol) of PCy$_3$ were then added to the reaction mixture before fitting the flask with a reflux condenser and heating the reaction to 100° C. under inert atmosphere for 17 hours. The reaction was allowed to cool and the mixture was filtered through a pad of silica that was washed with copious amounts of ethyl acetate. The solvent was removed in vacuo and crude was extracted with CH$_2$Cl$_2$ (3×50 mL). The organic layers were combined and washed with H$_2$O and brine and subsequently dried over Na$_2$SO$_4$ before being concentrated in vacuo and chromatographed (silica gel, 9:1 CH$_2$Cl$_2$/EtOAc then 1:1 CH$_2$Cl$_2$/EtOAc) to give amine 5 (720 mg, 68%). Analytical data for title compound: $^1$H NMR (400 MHz, CDCl$_3$) δ 8.07 (t, J=8.1, 2H), 7.85 (d, J=2.0 Hz, 1H), 7.80 (dd, J=8.6, 2.0 Hz, 1H), 7.32 (d, J=8.3 Hz, 1H), 7.24-7.16 (m, 2H), 6.87 (m, 1H), 6.83-6.78 (td, J=8.6, 1.0 Hz, 1H), 3.80 (s, 2H), 2.77 (s, 3H) (see FIG. 6A); $^{13}$C NMR (100 MHz, CDCl$_3$) δ 159.24, 147.13, 143.89, 137.08, 136.26, 131.07, 130.78, 129.19, 128.95, 127.51, 126.91, 126.78, 122.50, 118.89, 115.91, 25.53 (see FIG. 6B); HRMS (EI) calc. for [C$_{16}$H$_{14}$N$_2$]$^+$ 234.1157. found 234.1156; IR (NaCl) ν 3367, 3025, 2252, 1616, 1489, 1300, 1222, 1158, 835, 752 cm$^{-1}$.

Synthesis of Urea 6

Figure 7:
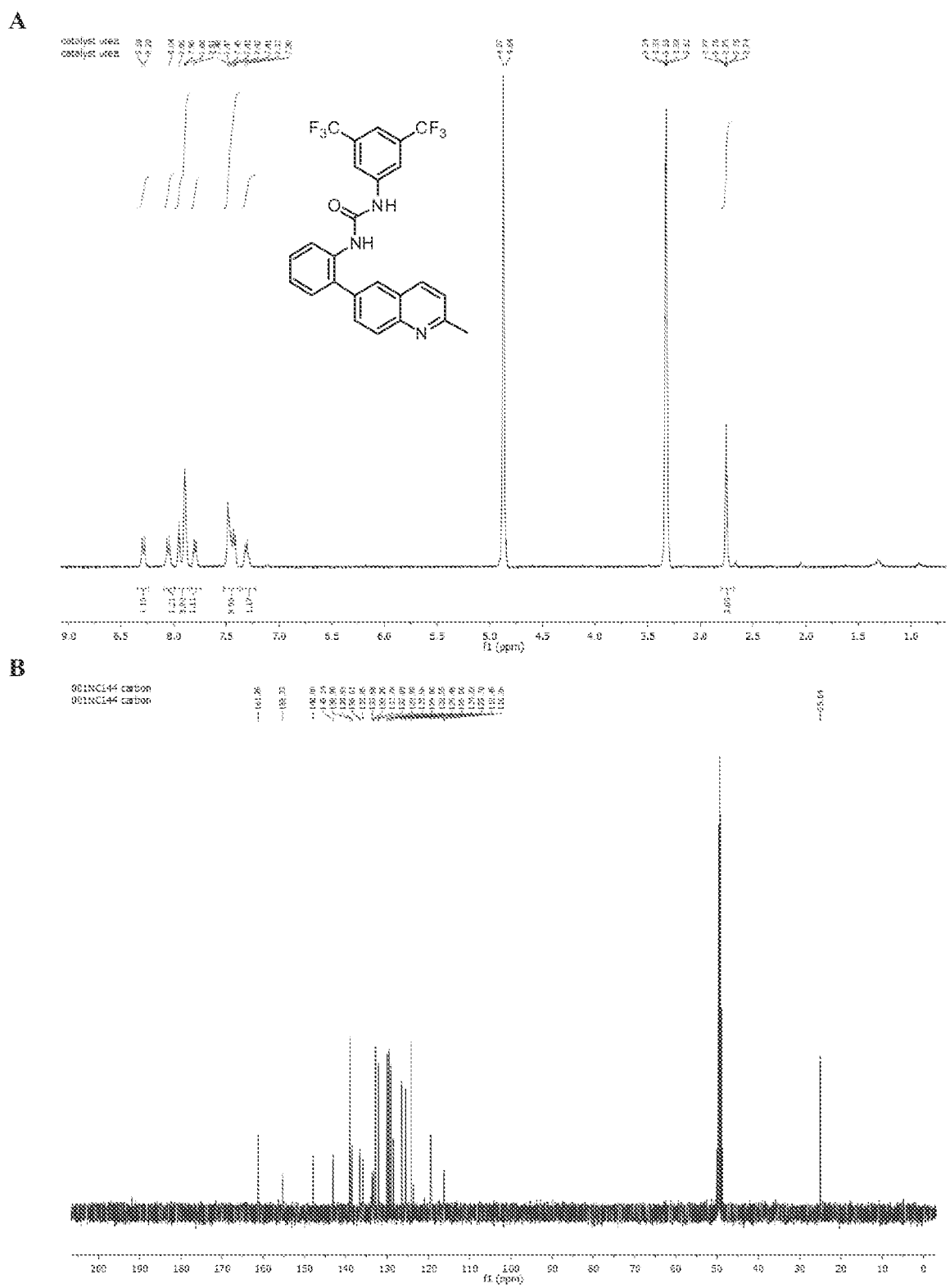
FIGS. 7A-B are the $^1$H-NMR (FIG. 7A) and $^{13}$C-NMR (FIG. 7B) spectra of urea 6.

To a stirred solution of amine 5 (720 mg, 3 mmol) in 20 mL CH$_2$Cl$_2$ was added 780 μL (4.6 mmol) of 3,5-Bis(trifluoromethyl)phenyl isocyanate. The reaction was allowed to stir overnight under argon atmosphere at room temperature. The solvent was removed in vacuo and the crude was chromatographed (silica gel, 9:1 $CH_2Cl_2$/EtOAc then 4:1 $CH_2Cl_2$/EtOAc) to obtain urea 6 (1.46 g, 98%). Analytical data for title compound: $^1$H NMR (400 MHz, MeOD) δ 8.29 (d, J=8.4 Hz, 1H), 8.05 (d, J=8.8 Hz, 1H), 7.95 (s, 1H), 7.92 (s, 3H), 7.81 (d, J=8.2 Hz, 1H), 7.54-7.36 (m, 3H), 7.31 (m, 1H), 2.75 (s, 3H) (see FIG. 7A); $^{13}$C NMR (100 MHz, MeOD) δ 161.26, 155.33, 148.00, 143.14, 138.90, 138.53, 136.61, 135.85, 133.58, 133.26, 132.78, 132.09, 129.98, 129.56, 129.08, 128.55, 126.45, 125.56, 124.22, 119.46, 116.26, 25.04 (see FIG. 7B); HRMS (EI) calc. for $[C_{25}H_{17}F_6N_3O]^+$ 489.1276. found 489.1281; IR (NaCl) ν 3342, 3152, 1724, 1661, 1501, 1418, 1252, 1144, 1067.

Synthesis of Aldehyde 7

A 50 mL round bottom flask was charged with 1.46 g (3.0 mmol) of urea 6 and 410 mg (3.7 mmol) of $SeO_2$. The quantity 15 mL of p-dioxane was added and the flask was fitted with a reflux condenser and heated to 80° C. for two hours. The reaction was allowed to cool to room temperature before filtering through a pad of celite. The solvent was removed in vacuo to yield pure aldehyde 7 (1.45 g, 97%). Analytical data for title compound: $^1$H NMR (400 MHz, MeOD) δ 10.18 (s, 1H), 8.56 (d, J=8.5 Hz, 1H), 8.33 (d, J=8.7 Hz, 1H), 8.15-8.03 (m, 2H), 8.00-7.84 (m, 4H), 7.48 (m, 3H), 7.36 (m, 1H) (see FIG. 8); $^{13}$C NMR (insoluble); HRMS (EI) calc. for $[C_{26}H_{19}F_6N_3O_3]^+$ 535.1331. found 535.1332; IR (NaCl) ν 3251, 3123, 2467, 1711, 1622, 1379, 1133.

Synthesis of Ligand 8

Figure 9:
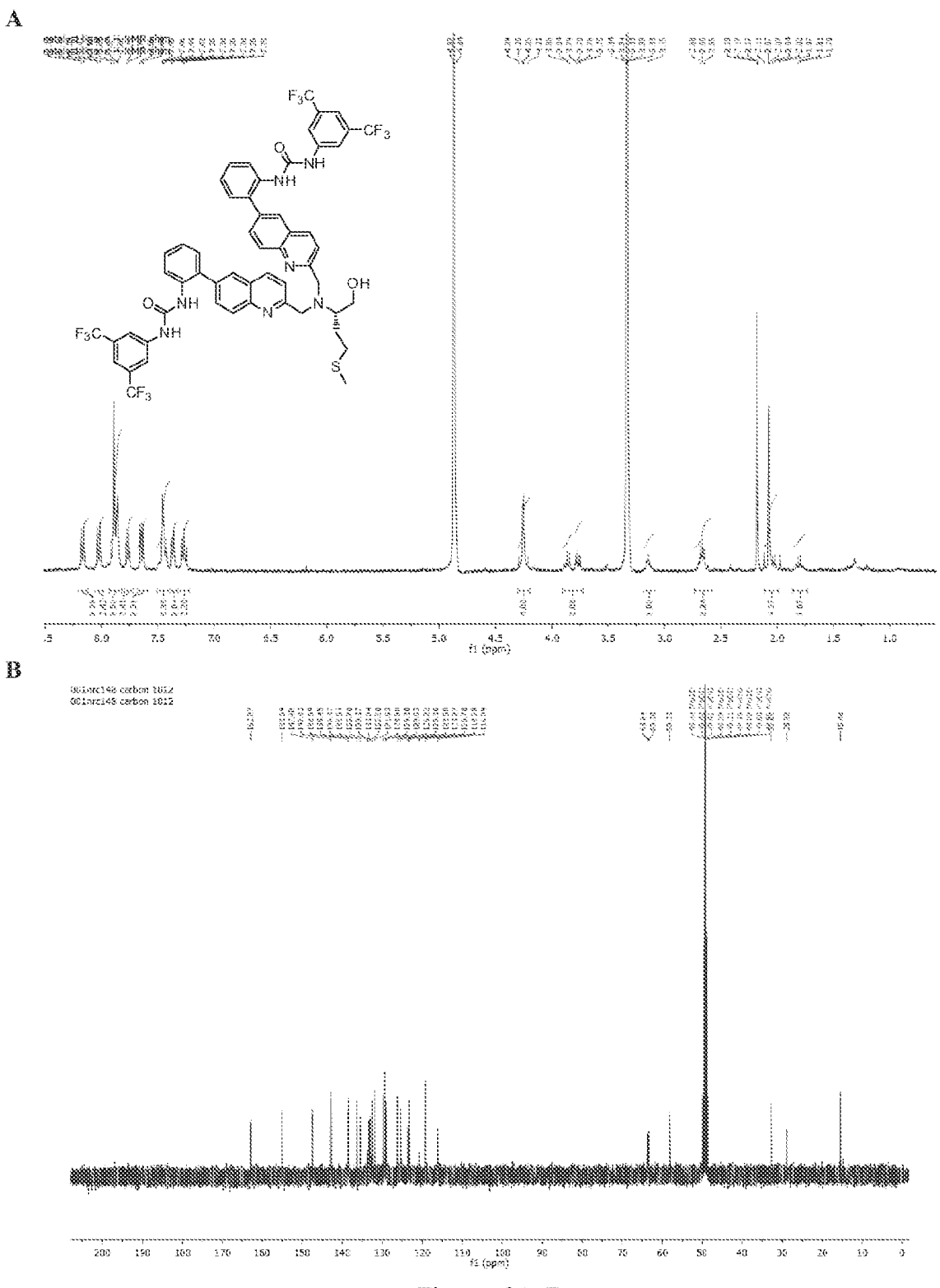
FIGS. 9A-B are the $^1$H-NMR (FIG. 9A) and $^{13}$C-NMR (FIG. 9B) spectra of ligand 8.

To a solution of 50 mg (0.37 mmol) L-methioninol in 2 mL MeOH at 0° C. was added a solution of 650 mg (1.3 mmol) aldehyde 7 in 10 mL MeOH. The mixture was stirred under argon for 10 minutes before 1.2 mL of AcOH and 80 mg (0.74 mmol) of 2-picoline borane were added at 0° C. The reaction was allowed to warm to room temperature and stirred for 16 hours before the solvent was removed in vacuo. The crude reaction mixture was then cooled to 0° C. and treated with 10% aq. HCl (10 mL) and allowed to stir at room temperature for 30 minutes. The mixture was then made alkaline using 25% aq. $Na_2CO_3$ (50 mL). Product was then extracted into EtOAc (3×50 mL) and organics were combined and washed with $H_2O$ and brine before drying over $Na_2SO_4$. Solvent was removed in vacuo and crude was chromatographed (silica gel, 1:1 EtOAc/$CH_2Cl_2$ then 10:1 $CH_2Cl_2$/MeOH) to obtain ligand 8 (386 mg, 94%). Analytical data for title compound: $^1$H NMR (400 MHz, MeOD) δ 8.17 (d, J=8.6 Hz, 2H), 8.02 (d, J=8.7 Hz, 2H), 7.89-7.86 (m, 9H), 7.76 (d, J=8.5 Hz, 2H), 7.65 (d, J=8.5 Hz, 2H), 7.51-7.39 (m, 5H), 7.37 (d, J=7.1 Hz, 2H), 7.26 (t, J=7.6 Hz, 2H), 4.25 (s, 4H), 3.91-3.72 (m, 2H), 3.15 (s, 1H), 2.73-2.58 (m, 2H), 2.07-1.97 (m, 4H), 1.80 (m, 1H) (see FIG. 9A); $^{13}$C NMR (100 MHz, MeOD) δ 162.87, 155.09, 147.48, 142.93, 138.69, 138.45, 136.37, 135.51, 133.37, 133.04, 132.50, 131.93, 129.80, 129.30, 129.03, 126.22, 125.36, 123.50, 123.27, 119.28, 116.09, 63.64, 63.38, 58.23, 32.82, 28.92, 15.48 (see FIG. 9B); HRMS (EI) calc. for $[C_{55}H_{43}F_{12}N_7O_3S]^+$ 1109.2956. found 1109.2952; IR (NaCl) ν 3127, 1645, 1499, 1384, 1287, 1150, 1088.

Example 3

Synthesis of Ambidextrous Catalyst Δ/Λ-1

Ambidextrous catalyst Δ/Λ-1 was synthesized as shown in Scheme 2 below.

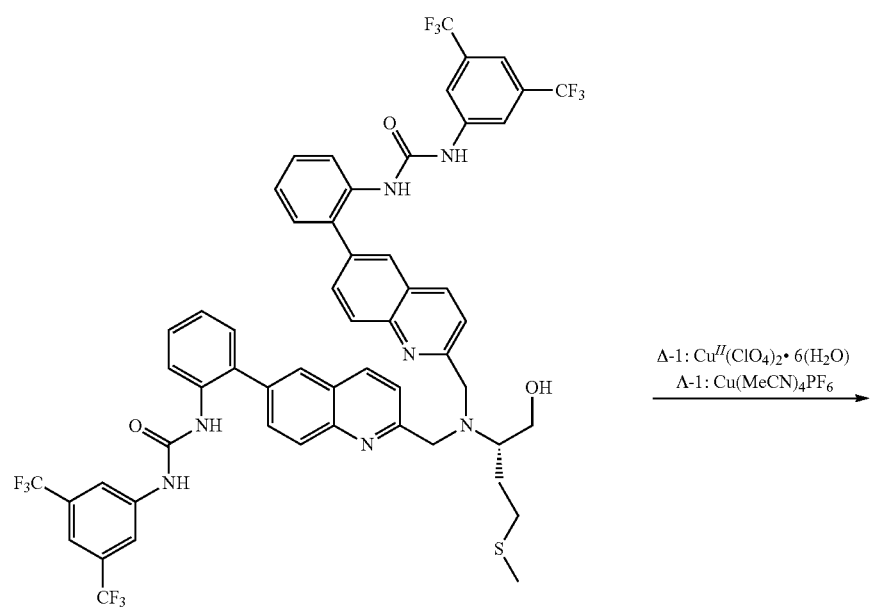

-continued

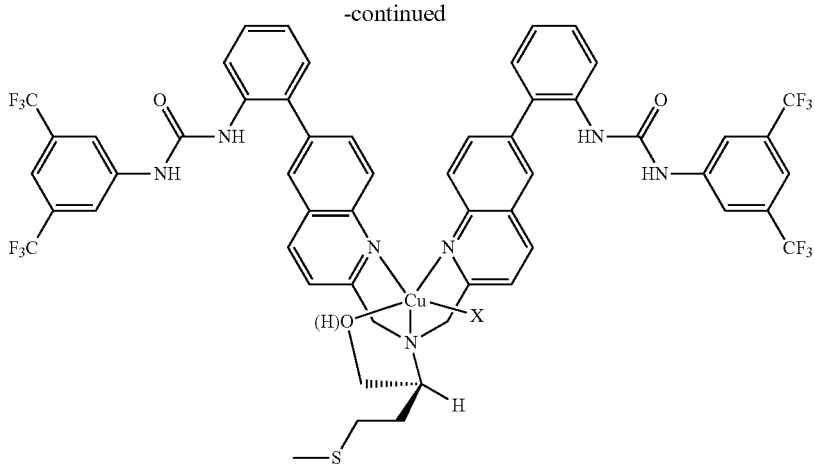

Δ-1

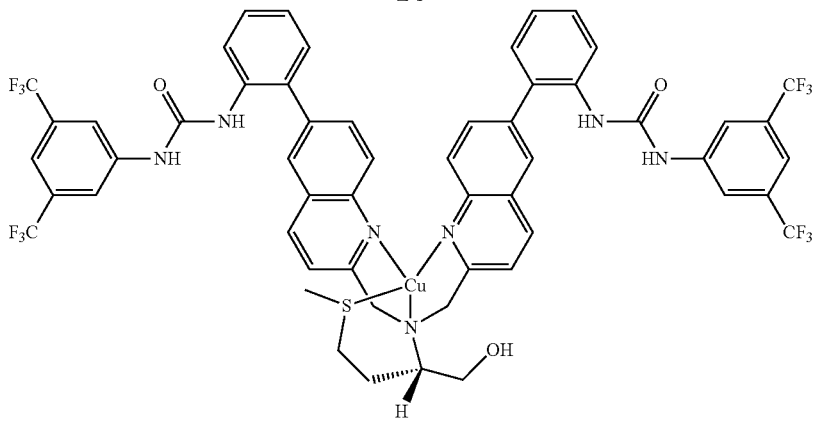

Λ-1

Synthesis of Catalyst Δ-1

A solution of ligand 8 (100 mg, 0.09 mmol) in 210 μL of MeOH was stirred at room temperature for 5 minutes before a solution of $Cu^{II}(ClO_4)_2 \cdot 6(H_2O)$ (40 mg, 1.0 mmol) in 300 μL of MeOH was added. The reaction was stirred at room temperature for one hour until a blue precipitate formed. The solid was obtained by filtration and washed with diethyl ether. The product was then recrystallized twice using acetonitrile to obtain $[Cu^{II}(8)](ClO_4)_2 \cdot 2(H_2O)$ (abb. as Δ-1) (101 mg, 80%) as a light blue solid. Analytical data for title compound: LRMS (EI): 1172 (M+), 622, 505 Anal. Calcd (mass %) for $C_{55}H_{47}Cl_2CuF_{12}N_7O_{13}S$: C, 46.90; H, 3.36; N, 6.96. Found C, 46.66; H, 2.99; N, 6.95.

Synthesis of Catalyst Λ-1

The quantity 197 mg (0.18 mmol) of ligand 8 was dissolved in 10 mL $CH_2Cl_2$ and purged with $N_2$ before placing into a glovebox. After 5 minutes 71 mg (0.19 mmol) of $Cu(MeCN)_4PF_6$ was added to the reaction mixture in the glovebox. The reaction was stirred for 30 minutes and the solvent was removed in vacuo to obtain $[Cu^I(8)]PF_6$ (abb. as Λ-1) (210 mg, 88%) as a yellow solid. LRMS (EI): 1172 (M+), 698, 505; $^1H$ NMR (400 MHz, MeOD) δ 8.70 (d, J=8.0 Hz, 1H), 8.52 (d, J=8.0 Hz, 1H), 8.41 (d, J=8.0 Hz, 1H), 8.36 (d, J=8.0 Hz, 1H), 7.96-7.93 (m, 3H), 7.85-7.81 (m, 2H), 7.72-7.63 (m, 6H), 7.58 (d, J=8.0 Hz, 1H), 7.46 (d, J=8.0 Hz, 1H), 7.38-7.18 (m, 9H), 4.36 (d, J=12.0 Hz, 1H), 4.0-3.99 (dd, J=4.0 Hz, 1H), 3.96 (d, J=4.0 Hz, 1H), 3.78-3.75 (m, 1H), 2.98-2.89 (m, 3H), 2.20 (s, 3H), 1.88-1.83 (m, 2H).

Alternative Synthesis of Catalyst Λ-1

Catalyst Λ-1 was also synthesized by reduction of Δ-1, as follows. Δ-1 (24 mg, 0.017 mmol) was dissolved in 1 mL of $CH_2Cl_2$. $NEt_3$ (4 μL, 0.034 mmol) and L-ascorbic acid (6 mg, 0.034 mmol) were then added to the mixture and stirred for 1 hour at room temperature. A color change from light blue to yellow can be observed after addition of ascorbic acid. The solvent was removed in vacuo and the solid was suspended in degassed $H_2O$ (2 mL) and filtered. The solid residue was washed with $H_2O$ and hexane before drying under reduced pressure. The yellow solid was then used as catalyst.

Example 4

Characterization of Catalyst Δ/Λ-1

Figure 10:
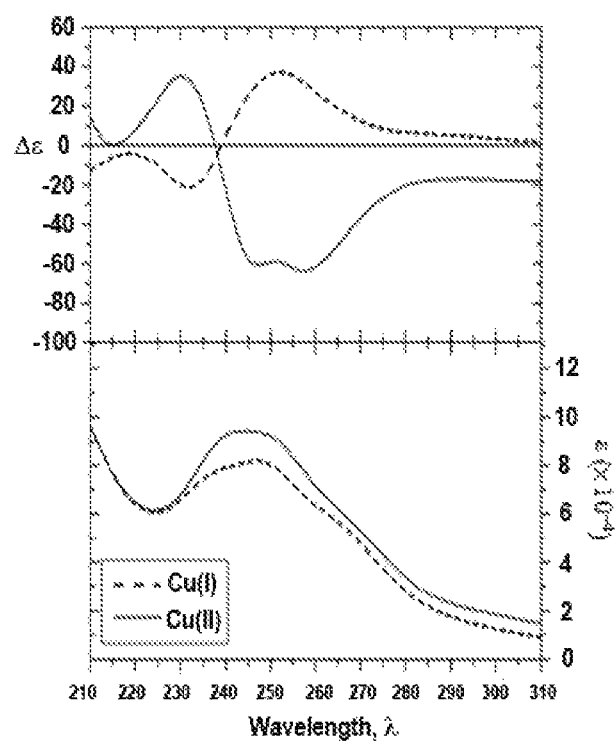
FIG. 10 shows the UV and circular dichroism spectra for ambidextrous catalyst Δ/Λ-1. The quinolines in Δ-1 form a right-handed propeller with counterclockwise chiral orientation and negative ECCD couplet because $Cu^{2+}$ prefers oxygen over sulfur.

Circular dichroism was used to evaluate the copper complexes of Δ/Λ-1. As shown in FIG. 10, the absorption spectrum of Δ-1 ($Cu^2$) shows a flattened peak suggesting transitions of similar intensity near 247 and 258 nm with trough at 251 nm, null near 238 nm, and peak near 230 nm. The Λ-1 ($Cu^+$) compound shows a broad peak near 248 nm and associated peak, null, and trough at 252, 239, and 232 nm, respectively (Zahn & Canary, *J. Am. Chem. Soc'y* 124:9204 (2002), which is hereby incorporated by reference in its entirety). Overall, the CD spectra give significant mirror image ECCD

Example 5

Michael Addition Using Ambidextrous Catalyst Δ/Λ-1

Δ/Λ-1 was used to catalyze the Michael addition of diethyl malonate to trans-β-nitrostyrene, as shown in Scheme 3 below.

Scheme 3

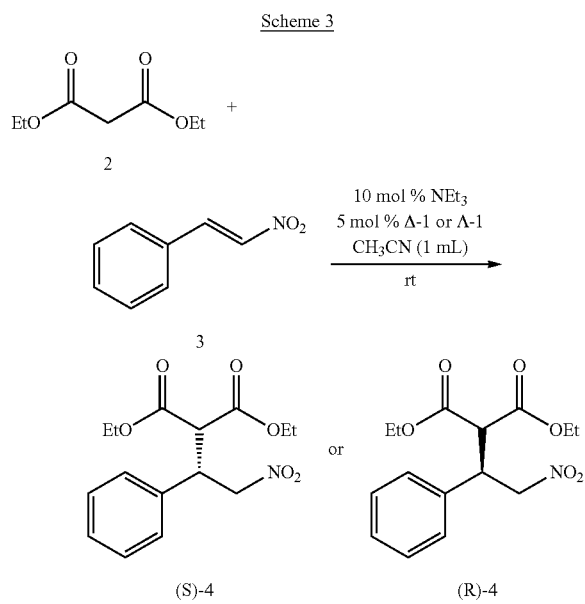

Figure 12A:
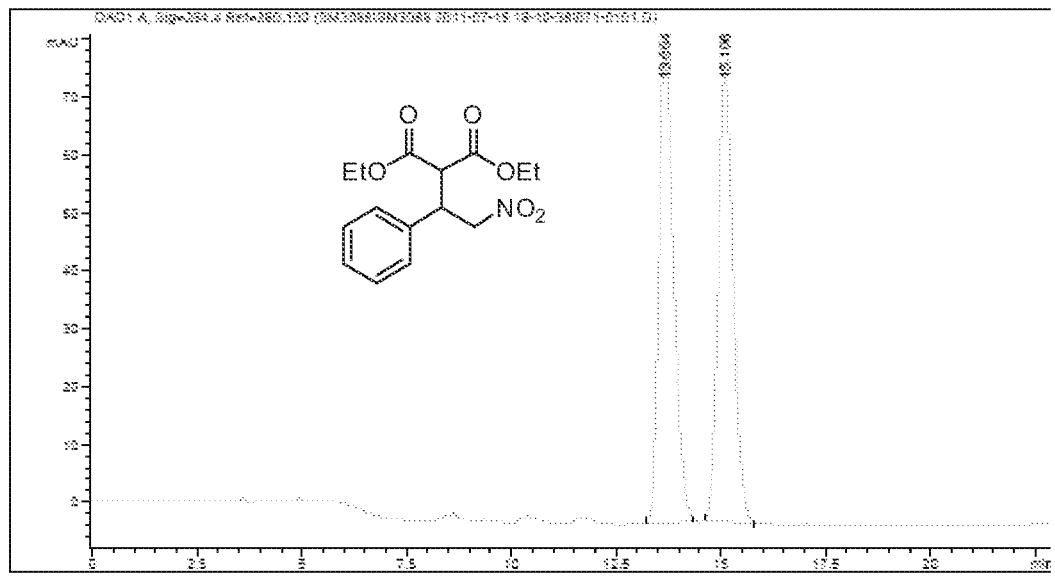

Synthesis of (S)-4 trans-β-Nitrostyrene (3) (50 mg, 0.34 mmol), diethyl malonate (2) (102 μL, 0.67 mmol), and acetonitrile (1 mL) were added to a scintillation vial equipped with a magnetic stir bar. Catalyst Δ-1 (24 mg, 0.017 mmol) was added to the vial and stirred for 5 minutes until finally NEt₃ (4 μL, 0.034 mmol) was added to activate the reaction. The reaction was stirred for 24 hours at room temperature at which point the solvent was removed in vacuo. The crude was then chromatographed (silica gel, 15:85 EtOAc/hexane) to obtain (S)-4 (58 mg, 55%). Analytical data for title compound: $[\alpha]_D^{25}$=+5.8 (c 1.03, CHCl₃, 72% ee (S)); ¹H NMR (400 MHz, CDCl₃) δ 7.29-7.10 (m, 5H), 4.88-4.73 (m, 2H), 4.21-4.07 (m, 3H), 3.92 (q, J=7.1 Hz, 2H), 3.73 (d, J=9.4 Hz, 1H), 1.17 (t, J=8.2, 3H), 0.96 (t, J=8.2, 3H) (see FIG. 11A); ¹³C NMR (100 MHz, CDCl₃) δ 167.43, 166.79, 136.22, 128.91, 128.33, 128.00, 77.63, 62.13, 61.86, 54.97, 42.96, 13.95, 13.72 (see FIG. 11B); HRMS (EI) calc. for $[C_{15}H_{19}NO_6]^+$ 309.1212. found 309.1196; HPLC (Chiralcel OD, hexane/ethanol=97/3, 1.00 mL/min, λ=210 nm, retention times: (S) (Major) 13.3 min, (R) (Minor) 14.4 min) (see FIGS. 12A-B).

Synthesis of (R)-4

Figure 13:
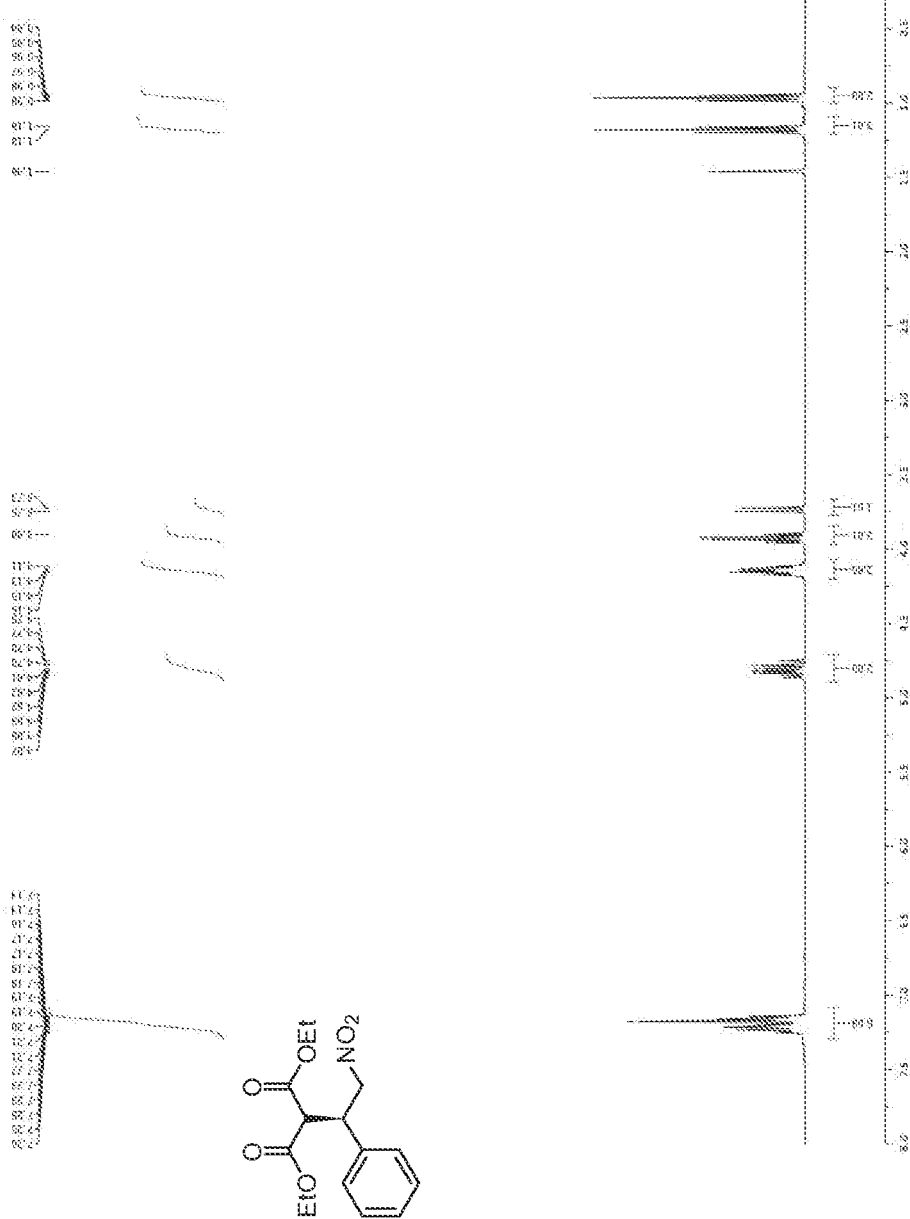
FIG. 13 is the $^1$H-NMR spectra of (R)-4.

The same procedure was used as for the synthesis of (S)-4 except catalyst Λ-1 (22 mg, 0.017 mmol) was used as the catalyst. Analytical data for title compound: $[\alpha]_D^{25}$=−4.9 (c 1.00, CHCl₃, 70% ee (R)); ¹H NMR (400 MHz, CDCl₃) δ 7.29-7.10 (m, 5H), 4.88-4.73 (m, 2H), 4.21-4.07 (m, 3H), 3.92 (q, J=7.1 Hz, 2H), 3.73 (d, J=9.4 Hz, 1H), 1.17 (t, J=8.2, 3H), 0.96 (t, J=8.2, 3H) (see FIG. 13); ¹³C NMR (100 MHz, CDCl₃) δ 167.43, 166.79, 136.22, 128.91, 128.33, 128.00, 77.63, 62.13, 61.86, 54.97, 42.96, 13.95, 13.72; HRMS (EI) calc. for $[C_{15}H_{19}NO_6]^+$ 309.1212. found 309.1196; HPLC (Chiralcel OD, hexane/ethanol=97/3, 1.00 mL/min, λ=210 nm, retention times: (S) (Minor) 13.3 min, (R) (Major) 14.4 min) (see FIGS. 12A and 12C).

Example 6

Solvent Screen

The ability of Δ/Λ-1 to catalyze the Michael addition of diethyl malonate to trans-β-nitrostyrene in different solvents was evaluated. All reactions were carried out using diethylmalonate (0.68 mmol, 2 equiv), β-nitrostyrene (0.34 mmol, 1 equiv), and NEt₃ (0.034 mmol, 0.1 equiv) in solvent (1 mL) with 5 mol % catalyst Δ-1 or Λ-1 at room temperature for 24 hours. The results are shown in Table 1 below.

TABLE 1

| | Solvent dependence of catalyzed reaction | | | |
| | Δ-1 | | Λ-1 | |
| Solvent | % e.e. of (S)-4[a] | % yield of 4[b] | % e.e. of (R)-4 | % yield of 4 |
|---|---|---|---|---|
| Toluene | 24 | 55 | 51 | 33 |
| THF | 48 | 33 | 57 | 78 |
| MeCN | 72 | 55 | 70 | 40 |
| CHCl₃ | 30 | 40 | 68 | 34 |
| CH₂Cl₂ | 46 | 44 | 74 | 43 |
| Hexane | 51 | 30 | 60 | 30 |

[a]Determined by chiral HPLC analysis
[b]Isolated yields

Example 7

Base Screen

The ability of Δ/Λ-1 to catalyze the Michael addition of diethyl malonate to trans-β-nitrostyrene in different bases was evaluated. All reactions were carried out using diethylmalonate (0.68 mmol, 2 equiv), β-nitrostyrene (0.34 mmol, 1 equiv), and base (0.034 mmol, 0.1 equiv) in MeCN (1 mL) with 5 mol % catalyst Δ-1 or Λ-1 at room temperature for 24 hours. The results are shown in Table 2 below.

TABLE 2

| | Base screen for different complex oxidation states | | | |
| | Δ-1 | | Λ-1 | |
| Base | % e.e. of (S)-4[a] | % yield of 4[b] | % e.e. of (R)-4 | % yield of 4 |
|---|---|---|---|---|
| NEt₃ | 72 | 55 | 70 | 40 |
| DIPEA | 70 | 38 | 56 | 32 |
| DABCO | 66 | 44 | 30 | 48 |
| DBU | 34 | 40 | 7 | 34 |
| DMAP | 57 | 21 | 31 | 32 |

[a]Determined by chiral HPLC analysis
[b]Isolated yields

Example 8

Loading, Concentration, and Temperature

The effects of loading, concentration, and temperature on the ability of Δ-1 to catalyze the Michael addition of diethyl malonate to trans-β-nitrostyrene was evaluated. All reactions were carried out using diethylmalonate (0.68 mmol, 2 equiv), β-nitrostyrene (0.34 mmol, 1 equiv), and NEt₃ (0-10 mol %) in MeCN (1 mL) with catalyst Δ-1 at room temperature for 24 hours unless otherwise noted. The results are shown in Table 3 below.

TABLE 3

Effects of concentration, loading, and temperature $$EtO-C(=O)-CH_2-C(=O)-OEt \quad + \quad Ph-CH=CH-NO_2 \xrightarrow[CH_3CN (1 mL)]{x \text{ mol } \% \text{ NEt}_3, \; y \text{ mol } \% \text{ }\Delta\text{-1}} (S)\text{-}4$$

| Entry | x | y | Conc Δ-1 (mM) | % e.e.[a] | % yield of (S)-4[b] |
|---|---|---|---|---|---|
| 1 | 10 | 5 | 17 | 72 | 55 (75)[e] |
| 2 | 10 | 5 | 34 | 70 | 50 |
| 3 | 10 | 10 | 34 | 72 | 39 |
| 4[c] | 10 | 5 | 34 | 74 | 52 |
| 5 | 2 | 0.5 | 1.7 | 62 | 67 |
| 6 | 10 | 0 | n/a | <1 | 18 |
| 7 | 0 | 5 | 17 | n/a | <1 |
| 8[d] | 10 | 5 | 17 | 20 | 44 |

[a]Determined by chiral HPLC analysis
[b]Isolated yield
[c]Reaction at 0° C.
[d]Reaction carried out with free ligand
[e]NMR yield Example 9

In Situ Reconfiguration of Δ-1 to Λ-1

The effect if in situ reconfiguration of Δ-1 to Λ-1 on the ability of Λ-1 to catalyze the Michael addition of diethyl malonate to trans-β-nitrostyrene was evaluated. Ascorbate (6 mg, 0.034 mmol), NEt₃ (4 µl, 0.034 mmol), and Δ-1 (24, 0.017 mmol) were stirred together and the resulting Λ-1 complex was isolated after an hour by precipitation. The conjugate addition reaction was then carried out using diethylmalonate (0.67 mmol, 2 equiv), β-nitrostyrene (0.34 mmol, 1 equiv), and NEt₃ (10 mol %) in MeCN (1 mL) with 5 mol % in situ reduced Λ-1 at room temperature for 24 hours. The results are shown in Table 4 below.

TABLE 4

Effects of in situ reconfiguration

| Λ-1 | % e.e. of (R)-4[a] | % yield of 4[b] |
|---|---|---|
| Synthesized from ligand 8 | 70[c] | 40[c] |
| Reduced in situ from Δ-1 | 71 | 43 |

[a]Determined by chiral HPLC analysis
[b]Isolated yields
[c]See Example 6, Table 1

Discussion of Examples 1-9

Figure 14:
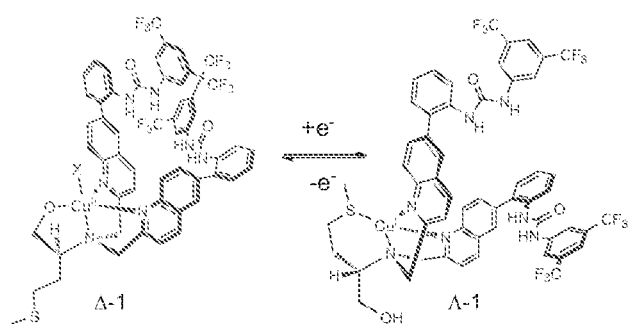
FIG. 14 illustrates the redox-triggered switching between Δ-1 and Λ-1. CD (L mol$^{-1}$ cm$^{-1}$) and UV (L mol$^{-1}$ cm$^{-1}$) of Δ/Λ-1 (59 uM, acetonitrile).

Previous studies described redox responsive coordination complexes capable of helical inversion (Zahn & Canary, Science 288:1404 (2000); Canary et al., Chem. Commun. 46:5850 (2010), which are hereby incorporated by reference in their entirety). Complexes derived from methionine or cysteine were shown to undergo inner sphere ligand rearrangement upon one electron oxidation or reduction of copper. The rearrangement was coupled to the orientation of two quinoline rings and affording right Δ, $Cu^{2+}$) or left Λ, $Cu^+$)-handed orientations as evidenced in solution by exciton-coupled circular dichroism (see FIG. 14) (Berova & Nakanishi, "Exciton Chirality Method: Principles and Applications," in CIRCULAR DICHROISM: PRINCIPLES AND APPLICATIONS 337-82 (Nina Berova et al. eds., 2d ed. 2000), which is hereby incorporated by reference in its entirety). As described in Examples 1-9 herein, the attachment of catalytic moieties to the quinoline units of tripodal ligands derived from L-methioninol for asymmetric catalysis were examined. In such a system, the copper ion inner coordination sphere would not be involved in catalysis but would serve to modulate the asymmetric orientation of the catalytic groups, which in turn could potentially catalyze organic reactions in both oxidation states to produce either enantiomer product from a single enantiomer of the ligand. Such a redox reconfigurable "ambidextrous" chiral catalyst capable of delivering either enantiomer of a nitro Michael addition product dependent on the oxidation state of a single copper atom is reported herein.

For catalyst Δ/Λ-1, urea groups were selected as reactive components due to their remarkably robust ability to behave as general acid catalysts via hydrogen bonding (Doyle & Jacobsen, Chem. Rev. 107:5713 (2007); Connon, Synlett 3:354 (2009), which are hereby incorporated by reference in their entirety). The catalyst ligand was synthesized using commercially available L-methioninol in five steps, as described in Example 2. The first step of the synthesis is a Miyaura borylation (Ishiyama et al., "Palladium(0)-Catalyzed Cross-Coupling Reaction of Alkoxydiboron with Haloarenes: A Direct Procedure for Arylboronic Esters," J. Org. Chem. 60:7505-10 (1995), which is hereby incorporated by reference in its entirety) of 6-bromo-2-methylquinoline followed by Suzuki coupling (Kudo et al., "A Versatile Method for Suzuki Cross-Coupling Reactions of Nitrogen Heterocycles," Angew. Chem. Int'l Ed. Engl. 45:1282-84 (2006), which is hereby incorporated by reference in its entirety) of 2-bromoaniline. Condensation of an isocyanate with amine 5 forms urea 6 in high yield. Oxidation with selenium dioxide followed by reductive amination of quinoline 7 with methioninol forms the final ligand 8. The five step synthesis of ligand 8 proceeds with an overall 61% yield. As described in Example 3, Cu(I) or Cu(II) salts are added to afford the catalyst complex.

Exciton chirality data establish that the complex was capable of helical chirality inversion, similar to the scaffold from which it was built. FIG. 10 shows the UV and CD spectra of isolated copper complexes. Electronic spectra of the copper complexes of Δ/Λ-1 (FIG. 10) are qualitatively similar to those reported for a similar unsubstituted quinoline derivative of L-methioninol (Barcena et al., *Org. Lett.* 5:709 (2003), which is hereby incorporated by reference in its entirety) but display additional features, most likely due to the presence of additional aromatic substituents in Δ/Λ-1 that may absorb in the UV wavelength region of the spectra. The absorption spectrum of Δ-1 ($Cu^2$) shows a flattened peak suggesting transitions of similar intensity near 247 and 258 nm. The transition near 247 nm is likely due to the $^1B_b$ transition with transition dipole oriented in the longitudinal direction crossing both rings and giving rise to an exciton couplet in the CD spectrum with trough at 251 nm, null near 238 nm, and peak near 230 nm. The latter is likely due to a π-π* transition involving the quinoline and attached phenyl ring. A possibly related additional trough appears in the CD spectrum near 260. The Λ-1 ($Cu^+$) compound shows a broad peak near 248 nm and associated peak, null, and trough at 252, 239, and 232 nm, respectively (Zahn & Canary, *J. Am. Chem. Soc'y* 124:9204 (2002), which is hereby incorporated by reference in its entirety). Overall, the CD spectra give significant mirror image ECCD character for the Δ-1 and Λ-1 complexes, consistent with inversion of the asymmetric orientation of the chromophores.

Encouraged by spectroscopic evidence indicating helical chirality inversion, the catalytic behavior of Δ-1 was assessed as described in Example 5. The Michael addition of diethyl malonate to trans-β-nitrostyrene has high synthetic utility as such Michael adducts (Hynes et al., *Org. Lett.* 10:1389 (2008), which is hereby incorporated by reference in its entirety) have previously shown to be amenable to catalysis by several thio(urea) organocatalysts (Okino et al., *J. Am. Chem. Soc'y* 127:119 (2005); McCooey & Connon, *Angew. Chem. Int'l Ed.* 44:6367 (2005); Takemoto, *Chem. Pharm. Bull.* 58:593 (2010); Okino et al., *J. Am. Chem. Soc'y* 125: 12672 (2003), which are hereby incorporated by reference in their entirety). It was envisioned that the urea moieties of Δ-1 and Λ-1 should lead to nearly enantiomeric transition states allowing the user to choose between (S)-4 or (R)-4 simply by choosing the redox state of the copper ion.

As described in Example 6, to test the catalytic ability of Δ-1, a solvent screen was performed using 1 mL of solvent, 10 mol % $NEt_3$, and 5 mol % catalyst Δ-1. Of the solvents tested, acetonitrile provided the highest yield (55%) and ee (72%) of product (S)-4. Significantly, in the presence of Δ-1 all solvents screened yielded product (S)-4. The same reaction was then tested using 5 mol % of Λ-1 as the catalyst, demonstrated a preference for enantiomeric product (R)-4 in all of the solvents tested. Remarkably, a similar ee (70%) was obtained in acetonitrile compared to the result with Δ-1.

As described in Example 7, several amine bases that gave the same enantiomer product were also examined, with more nucleophilic bases affording lower yields and ee. This may be due to competitive catalysis of the competing anionic polymerization of the trans-β-nitrostyrene starting material (Carter et al., *J. Polym. Sci. Pol. Chem.* 16:937 (1978), which is hereby incorporated by reference in its entirety).

The effects of catalyst loading, concentration, and temperature were then tested, as described in Example 8. Changes in temperature and concentration appeared to have little effect on the ee and yield of the reaction. Interestingly, increasing the loading of the catalyst to 10 mol % (Table 3, entry 3) caused no change in enantioselectivity. The catalyst still proved to be effective at 0.5 mol % loading (Table 3, entry 5), producing (S)-4 at 62% ee. The yield in this case may benefit from the lower concentration of base used. Control experiments indicate that the free ligand catalyzes the reaction (Table 3, entry 8), which is consistent with electrophilic catalysis provided by the urea groups and suggests that the copper is not involved directly in catalysis. Enantioselectivity is poor, however, in the absence of scaffolding provided by the copper ions.

As reducing agents such as ascorbate are capable of reconfiguring similar $Cu^{2+}$ complexes (Zahn & Canary, *J. Am. Chem. Soc'y* 124:9204 (2002), which is hereby incorporated by reference in its entirety), whether the Δ-1 complex could be reduced in situ to the Λ-1 form and be used to catalyze the same reaction was determined as described in Example 9. This was accomplished by stirring a mixture of ascorbate, $NEt_3$, and Δ-1 and isolating the resulting Λ-1 complex after an hour by precipitation. Nearly the same results were obtained when performing the conjugate addition with the in situ reduced complex. It is of interest that $NEt_3$ significantly solubilizes the $Cu^{2+}$ complex in the solvents tested.

The exact mechanism of catalysis in the reaction is not known. The urea groups are capable of binding both the diethyl malonate (2) and trans-β-nitrostyrene (3) reactants (Hamza et al., *J. Am. Chem. Soc'y* 128:13151 (2006); Cheong et al., *Chem. Rev.* 111:5042 (2011), which are hereby incorporated by reference in their entirety). Whether one or both urea groups play a role in the transition state is not yet clear. The ligand alone in the absence of copper ion is far more flexible than the complex and likely positions the urea groups further away from one another, yet the yield of the reaction is similar to that using the complex (see Table 3, entries 1 and 8). Monitoring the reaction by $^1H$ NMR revealed the half-life of the reaction catalyzed by free ligand to be half that of the Δ-1 complex. This may suggest that both urea groups do not act in concert in the transition state. Further mechanistic studies are underway.

An almost complete reversal of enantioselectivity was found when switching from Cu(II) to Cu(I) complex. This reversal of selectivity was observed in all solvents screened, albeit in not the same magnitude of difference. Various amine bases screened behaved similarly, although triethylamine gave the highest values of enantiomeric excess and enantiomeric difference. The Λ-1 gave identical ee whether prepared from a $Cu^+$ salt and 8 or if produced from Δ-1 followed by treatment with ascorbic acid and obtaining the $Cu^+$ complex via filtration. Thus, a catalyst such as Δ-1 could be sold commercially and could be used directly to produce one enantiomer in this reaction or pretreated with ascorbate for the production of the other enantiomer.

In summary, a new asymmetric urea catalyst that is capable of helical chirality inversion has been developed. ECCD techniques were used to establish that the switching event was dependent on the oxidation state of a coordinated copper atom. The enantioselectivity of the asymmetric conjugate addition of diethyl malonate to trans-β-nitrostyrene was found to depend on the helicity of the catalyst. The reconfiguration allows the user to select either product enantiomer without a requirement to produce both enantiomers of the catalyst. This could be beneficial by obviating the requirement for a parallel synthesis of the opposite enantiomer, offering economic or environmental benefit depending on scale, and especially if one enantiomer is derived from an unnatural chiral source. The ambidextrous nature of the catalyst is persistent using several different solvents and bases. Either complex is available by simply mixing ligand with the appropriate metal salt, or the Δ-1 complex can be reduced chemically to the less air stable Λ-1 complex and used to catalyze the conjugate addition.

Example 10

Modeling

Figure 15:
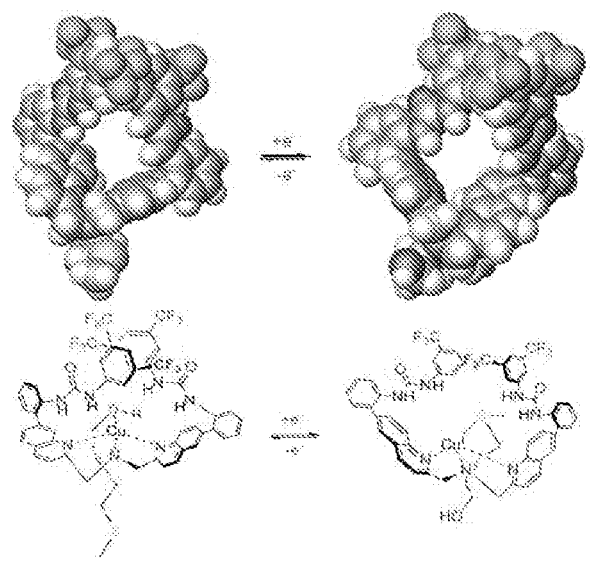
FIG. 15 is a space filling model of Δ-1 (left) and Λ-1 (right). In Λ-1 diphenylureas are rotated away from the alcohol forming a chiral cleft, while in Δ-1 diphenylureas are rotated towards alcohol.

FIG. 15, shows a space filled model of Δ-1 and Λ-1 derived by starting from X-ray coordinates of a closely related $Cu^{2+}$ complex (Holmes et al., "Stereodynamic Coordination Complexes. Dependence of Exciton Coupled Circular Dichroism Spectra on Molecular Conformation and Shape," *Monatsh. Chem.* 136:461-75 (2005), which is hereby incorporated by reference in its entirety) and manually attaching diphenylurea groups at appropriate locations using modeling software (Maestro, Schrödinger, Inc.). The biaryl linkage (Grein, "Twist Angles and Rotational Barriers of Biphenyl and Substituted Biphenyls," *J. Phys. Chem. A* 106:3823-27 (2002), which is hereby incorporated by reference in its entirety) allows the diphenylureas to access either of the two faces of the quinoline unit to which they are attached. As such, they can rotate towards or away from one another. The left side of FIG. 15 shows a view with rotations towards one another, yielding a highly asymmetrical cleft with the ureas clearly within distance for interaction with both reagents in the transition state of the addition reaction. On the other hand, it is possible that only one reagent (such as the nitrostyrene) binds in this cleft, directing approach by the nucleophile to a particular face.

Example 11

Conjugate Addition of Various Substrates

Examples 1-9 demonstrate the ability to achieve consistent enantiomeric excess in the malonate/nitrostyrene reaction and that the absolute configuration of the product depends only on allosteric consequences of the oxidation state (and thus the propeller helicity of the ligand) and not on counter ion, solvent, concentration, loading, or base. The ability of Δ/Λ-1 to catalyze the Michael addition of other nitrostyrenes and dimalonate esters was evaluated. All reactions were carried out using the indicated dimalonate ester (0.67 mmol, 2 equiv), the indicated nitrostyrene (0.34 mmol, 1 equiv), and $NEt_3$ (10 mol %) in MeCN (1 mL) with 5 mol % catalyst Δ-1 or Λ-1) at room temperature for 24 hours. The results are shown in Tables 5 and 6 below.

TABLE 5

Conjugate addition of nitrostyrenes and dimalonate esters

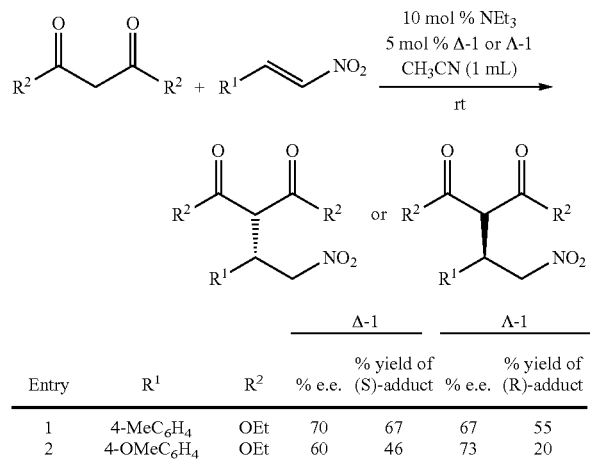

| | | | Δ-1 | | Λ-1 | |
|---|---|---|---|---|---|---|
| Entry | $R^1$ | $R^2$ | % e.e. | % yield of (S)-adduct | % e.e. | % yield of (R)-adduct |
| 1 | 4-MeC$_6$H$_4$ | OEt | 70 | 67 | 67 | 55 |
| 2 | 4-OMeC$_6$H$_4$ | OEt | 60 | 46 | 73 | 20 |

TABLE 5-continued

| 3 | 2,3-OMeC$_6$H$_3$ | OEt | 48 | 97 | 57 | 98 |
| 4 | 4-BrC$_6$H$_4$ | OEt | 24 | 45 | 72 | 48 |
| 5 | 4-OHC$_6$H$_4$ | OEt | 40 | 51 | 53 | 44 |
| 6 | Ph | OMe | 57 | 35 | 64 | 77 |
| 7 | Ph | i-PrO | 73 | 30 | 65 | 30 |

TABLE 6

Conjugate addition of nitrostyrenes and malonate esters that include a prochiral center

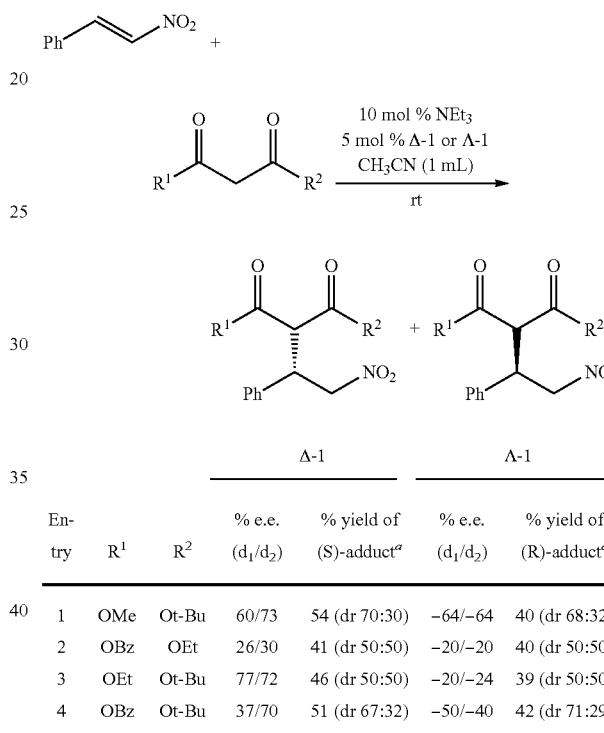

| | | | Δ-1 | | Λ-1 | |
|---|---|---|---|---|---|---|
| Entry | $R^1$ | $R^2$ | % e.e. ($d_1/d_2$) | % yield of (S)-adduct[a] | % e.e. ($d_1/d_2$) | % yield of (R)-adduct[a] |
| 1 | OMe | Ot-Bu | 60/73 | 54 (dr 70:30) | −64/−64 | 40 (dr 68:32) |
| 2 | OBz | OEt | 26/30 | 41 (dr 50:50) | −20/−20 | 40 (dr 50:50) |
| 3 | OEt | Ot-Bu | 77/72 | 46 (dr 50:50) | −20/−24 | 39 (dr 50:50) |
| 4 | OBz | Ot-Bu | 37/70 | 51 (dr 67:32) | −50/−40 | 42 (dr 71:29) |

[a]dr = diastereomeric ratios of the products

The conjugate addition of various nitrostyrenes has been tested using each oxidation state of the copper catalyst. Also, six other variations of dimalonate esters, including four that have a prochiral center, have been used as conjugate addition partners. As shown in Table 5 and Table 6, opposite enantioselectivity in each oxidation state of the catalyst was achieved in all cases. This demonstrates that ambidextrous catalyst Δ/Λ-1 can be used to catalyze the enantioselective addition of a wide range of substrates.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims that follow.

What is claimed:

1. A catalyst of Formula I:

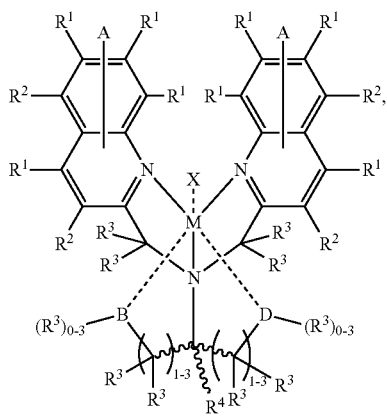

wherein:
- each $R^1$ is independently H; a lower alkyl; an aminyl; —$OR^6$ wherein $R^6$ is hydrogen or a lower alkyl; or the attachment point for A;
- each $R^2$ is independently H; a lower alkyl; an aminyl; or —$OR^6$ wherein $R^6$ is hydrogen or a lower alkyl;
- each $R^3$ and $R^4$ is independently hydrogen; an alkyl; an alkenyl; an alkynyl; an aminyl; a carbonyl; a cycloalkyl; a heterocyclyl; an aryl; a heteroaryl; an arylalkyl; an acyl; —$OR^5$ wherein $R^5$ is hydrogen, an alkyl, an alkenyl, an alkynyl, a cycloalkyl, a heterocyclyl, an aryl, a heteroaryl, an arylalkyl, or an acyl; or —$(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, or an acyl;
- each A is a catalytic moiety;
- B and D are atoms having different ionization potentials;
- M is a metal;
- X is absent, a solvent, or a counterion;
- each ∼∼∼ is a bond of undefined stereochemistry; and
- each - - - - is an optional bond with the proviso that:
  (i) the bond between M and B is present and the bond between M and D is absent; or
  (ii) the bond between M and B is absent and the bond between M and D is present.

2. The catalyst according to claim 1, wherein the catalyst is a catalyst of Formula I' or an enantiomer thereof:

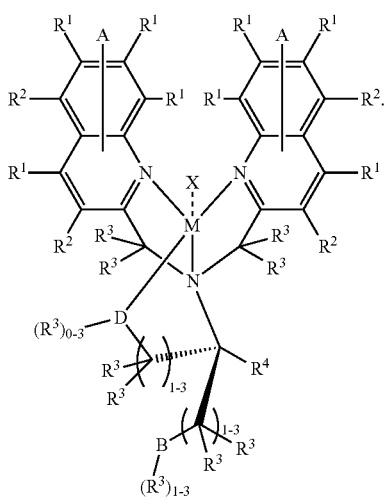

3. The catalyst according to claim 1, wherein the catalyst is a catalyst of Formula I" or an enantiomer thereof:

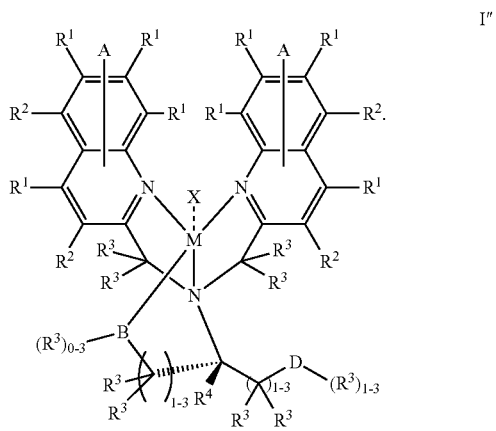

4. The catalyst according to claim 1, wherein $R^3$ is a lower alkyl.

5. The catalyst according to claim 1, wherein $R^4$ is hydrogen.

6. The catalyst according to claim 1, wherein each catalytic moiety is selected from the group consisting of (thio)ureas; guanidines, amides, phenols, carboxylic acids, and other hydrogen bond donating groups; and a moiety of formula -$E^1$-NH—C(=G)-NH-$E^2$, wherein $E^1$ and $E^2$ are each independently absent, an alkyl, an aryl, or a heteroaryl and G is O, S, NR, or —$N^+R_2$, wherein each R is independently hydrogen, an alkyl, an alkenyl, an alkynyl, an aminyl, a carbonyl, a cycloalkyl, a heterocyclyl, an aryl, a heteroaryl, an arylalkyl, or an acyl.

7. The catalyst according to claim 6, wherein each catalytic moiety is a moiety of formula -$E^1$-NH—C(=G)-NH-$E^2$.

8. The catalyst according to claim 1, wherein B or D is sulfur or selenium.

9. The catalyst according to claim 1, wherein B or D is oxygen.

10. The catalyst according to claim 1, wherein one of B and D is sulfur or selenium and the other of B and D is oxygen.

11. The catalyst according to claim 1, wherein M is Cu(I), Cu(II), Ag(I), Hg(II), Ni(II), Cd(II), Zn(II), Fe(II), Fe(III), Co(II), or another first row transition metal of oxidation state II or higher.

12. The catalyst according to claim 1, wherein the bond between M and B is present and the bond between M and D is absent.

13. The catalyst according to claim 1, wherein the bond between M and B is absent and the bond between M and D is present.

14. The catalyst according to claim 1, wherein the catalyst is a catalyst of Formula IA:

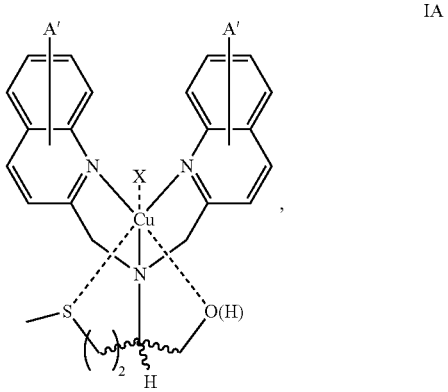

wherein each A' is independently a moiety of formula -E$^1$-NH—C(═O)—NH-E$^2$, wherein E$^1$ is an aryl or a heteroaryl and E$^2$ is an alkyl, an aryl, or a heteroaryl.

15. The catalyst according to claim 14, wherein the bond between the copper atom and the oxygen atom is present, and the bond between the copper atom and the sulfur atom is absent.

16. The catalyst according to claim 15, wherein the catalyst is a catalyst of Formula IB or an enantiomer thereof:

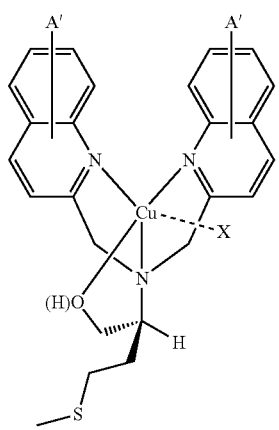

IB

17. The catalyst according to claim 16, wherein the catalyst is

18. The catalyst according to claim 14, wherein the bond between the copper atom and the oxygen atom is absent, and the bond between the copper atom and the sulfur atom is present.

19. The catalyst according to claim 18, wherein the catalyst is a catalyst of Formula IC or an enantiomer thereof:

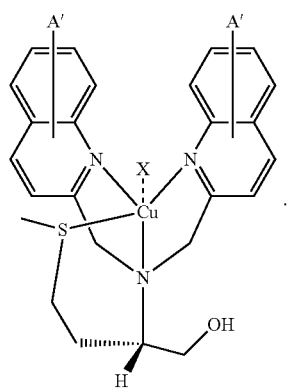

IC

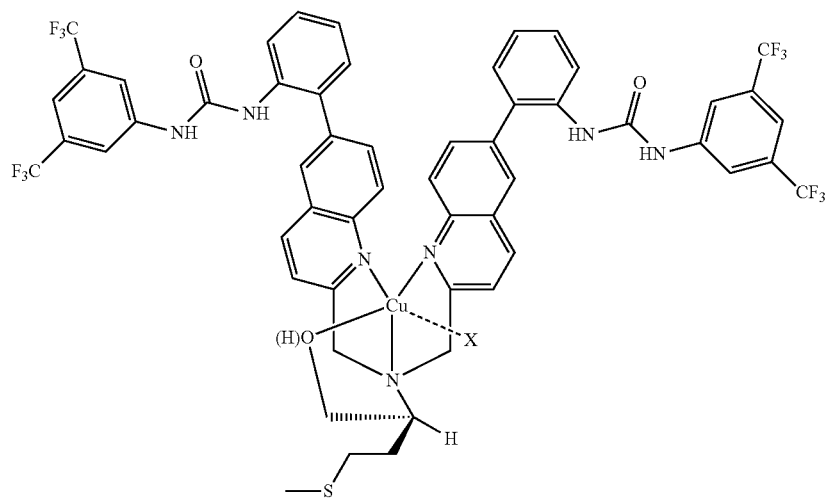

or the enantiomer thereof.

20. The catalyst according to claim 19, wherein the catalyst is

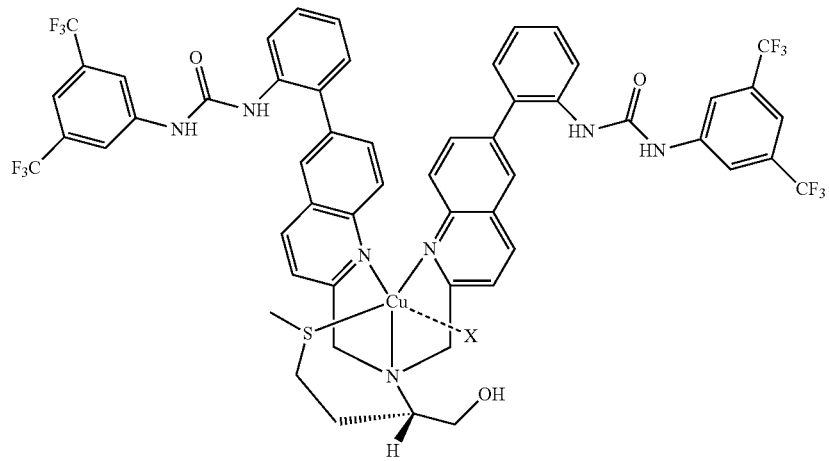

or the enantiomer thereof.

21. A method of producing a compound having a stereocenter, said method comprising:

reacting a starting compound in the presence of a catalyst according to claim 1 under conditions effective to produce the compound having a stereocenter.

22. The method according to claim 21, wherein said reacting involves carrying out a reaction selected from the group consisting of conjugate addition reactions, aldol reactions, and Diels-Alder reactions.

23. The method according to claim 22, wherein the reaction is a Michael addition reaction.

24. The method according to claim 21, wherein the compound can exist as one of two enantiomers and said reacting is carried out under conditions effective to preferentially produce one of the enantiomers over the other enantiomer.

25. The method according to claim 24, wherein the (S)-enantiomer is preferentially produced.

26. The method according to claim 24, wherein the (R)-enantiomer is preferentially produced.

27. A method of producing a compound having at least two stereocenters, said method comprising:

(i) reacting a starting compound in the presence of a first catalyst under conditions effective to produce a first product compound, the first product compound having at least one stereocenter; and (ii) reacting the first product compound or a subsequent reaction product thereof in the presence of a second catalyst under conditions effective to produce a second product compound, the second product compound having at least two stereocenters;

wherein the first catalyst and the second catalyst are each independently a catalyst of Formula I' or an enantiomer thereof, or a catalyst of Formula I" or an enantiomer thereof:

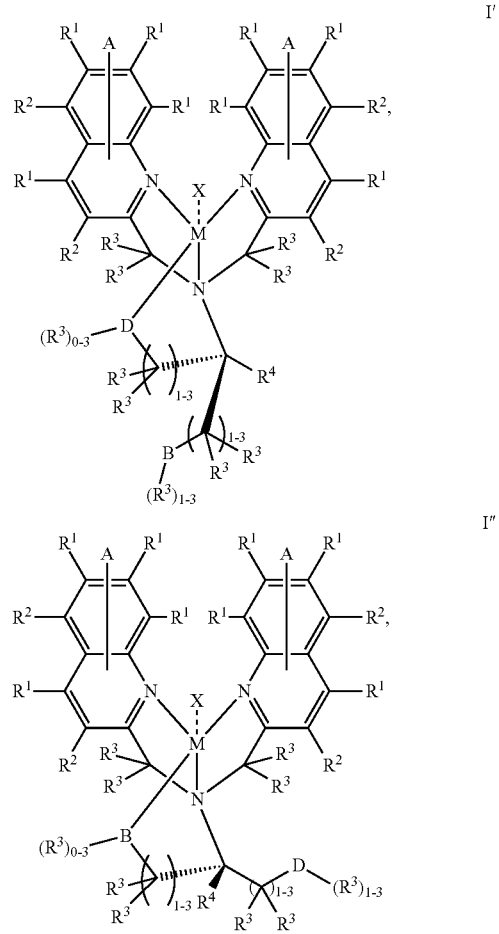

wherein:
each $R^1$ is independently H; a lower alkyl; an aminyl; —$OR^6$ wherein $R^6$ is hydrogen or a lower alkyl; or the attachment point for A;
each $R^2$ is independently H; a lower alkyl; an aminyl; or —$OR^6$ wherein $R^6$ is hydrogen or a lower alkyl;

each $R^3$ and $R^4$ is independently hydrogen; an alkyl; an alkenyl; an alkenyl; an aminyl; a carbonyl; a cycloalkyl; a heterocyclyl; an aryl; a heteroaryl; an arylalkyl; an acyl; —$OR^5$ wherein $R^5$ is hydrogen, an alkyl, an alkenyl, an alkenyl, a cycloalkyl, a heterocyclyl, an aryl, a heteroaryl, an arylalkyl, or an acyl; or —$(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, or an acyl;

each A is a catalytic moiety;

B and D are atoms having different ionization potentials;

M is a metal;

X is absent, a solvent, or a counterion; and

- - - - is an optional bond.

28. The method according to claim 27, wherein the first catalyst and the second catalyst both preferentially produce an (S)-stereocenter.

29. The method according to claim 27, wherein the first catalyst and the second catalyst both preferentially produce an (R)-stereocenter.

30. The method according to claim 27, wherein one of the first catalyst and the second catalyst preferentially produces an (S)-stereocenter and the other of the first catalyst and the second catalyst preferentially produces an (R)-stereocenter.

31. The method according to claim 30, wherein the second catalyst is produced by reducing the first catalyst.

32. The method according to claim 31, wherein said reducing is carried out in situ.

33. The method according to claim 30, wherein the second catalyst is produced by oxidizing the first catalyst.

34. The method according to claim 33, wherein said oxidizing is carried out in situ.

35. The method according to claim 27, said method comprising:
   (i) reacting the starting compound in the presence of the first catalyst under conditions effective to produce the first product compound,
   (ii) reacting the first product compound in the presence of the second catalyst under conditions effective to produce a second product compound, the second product compound comprising at least two stereocenters,
   (iii) optionally reacting the product of the immediately previous reacting step in the presence of an additional catalyst under conditions effective to produce a product compound comprising an additional stereocenter, and
   (iv) optionally repeating step (iii) one or more times;

wherein each additional catalyst is independently a catalyst of Formula I' or enantiomer thereof or a catalyst of Formula I" or enantiomer thereof.

36. The catalyst according to claim 1, wherein:

each catalytic moiety is selected from the group consisting of (thio)ureas; guanidines, amides, phenols, carboxylic acids, and other hydrogen bond donating groups; and a moiety of formula -$E^1$-NH—C(=G)-NH-$E^2$, wherein $E^1$ and $E^2$ are each independently absent, an alkyl, an aryl, or a heteroaryl and G is O, S, NR, or —$N^+R_2$, wherein each R is independently hydrogen, an alkyl, an alkenyl, an alkynyl, an aminyl, a carbonyl, a cycloalkyl, a heterocyclyl, an aryl, a heteroaryl, an arylalkyl, or an acyl; and B and D are atoms having a difference in ionization potential of at least about 50 kJ/mol.

37. The catalyst according to claim 1, wherein:

each catalytic moiety is a moiety of formula -$E^1$-NH—C(=O)—NH-$E^2$, wherein $E^1$ is an aryl or a heteroaryl and $E^2$ is an alkyl, an aryl, or a heteroaryl;

B and D are selected from the group consisting of sulfur, selenium, and oxygen; and M is Cu(I), Cu(II), Ag(I), Hg(II), Ni(II), Cd(II), Zn(II), Fe(II), Fe(III), Co(II), or another first row transition metal of oxidation state II or higher.

38. The method according to claim 27, wherein:

each catalytic moiety is selected from the group consisting of (thio)ureas; guanidines, amides, phenols, carboxylic acids, and other hydrogen bond donating groups; and a moiety of formula -$E^1$-NH—C(=G)-NH-$E^2$, wherein $E^1$ and $E^2$ are each independently absent, an alkyl, an aryl, or a heteroaryl and G is O, S, NR, or —$N^+R_2$, wherein each R is independently hydrogen, an alkyl, an alkenyl, an alkynyl, an aminyl, a carbonyl, a cycloalkyl, a heterocyclyl, an aryl, a heteroaryl, an arylalkyl, or an acyl; and B and D are atoms having a difference in ionization potential of at least about 50 kJ/mol.

39. The method according to claim 27, wherein:

each catalytic moiety is a moiety of formula -$E^1$-NH—C(=O)—NH-$E^2$, wherein $E^1$ is an aryl or a heteroaryl and $E^2$ is an alkyl, an aryl, or a heteroaryl;

B and D are selected from the group consisting of sulfur, selenium, and oxygen; and M is Cu(I), Cu(II), Ag(I), Hg(II), Ni(II), Cd(II), Zn(II), Fe(II), Fe(III), Co(II), or another first row transition metal of oxidation state II or higher.

* * * * *